(12) United States Patent
Aldred et al.

(10) Patent No.: US 11,107,992 B2
(45) Date of Patent: Aug. 31, 2021

(54) CROSS-LINKABLE CHARGE TRANSPORT MATERIALS

(71) Applicant: LOMOX LIMITED, Congleton (GB)

(72) Inventors: Matthew P. Aldred, Congleton (GB); Luke William Judd, Congleton (GB); Clare Foden, Congleton (GB)

(73) Assignee: Lomox Limited, Congleton (GB)

( * ) Notice: Subject to any disclaimer, the term of this patent is extended or adjusted under 35 U.S.C. 154(b) by 384 days.

(21) Appl. No.: 15/768,669

(22) PCT Filed: Oct. 13, 2016

(86) PCT No.: PCT/GB2016/053171
§ 371 (c)(1),
(2) Date: Apr. 16, 2018

(87) PCT Pub. No.: WO2017/064490
PCT Pub. Date: Apr. 20, 2017

(65) Prior Publication Data
US 2018/0309064 A1  Oct. 25, 2018

(30) Foreign Application Priority Data

Oct. 16, 2015  (GB) ..................................... 1518366

(51) Int. Cl.
*H01L 51/00* (2006.01)
*H01L 51/50* (2006.01)
(Continued)

(52) U.S. Cl.
CPC ........ *H01L 51/0039* (2013.01); *C07C 217/80* (2013.01); *C07D 207/452* (2013.01);
(Continued)

(58) Field of Classification Search
CPC ............. H01L 51/0039; H01L 51/0034; H01L 51/0062; H01L 51/5056; H01L 51/0059;
(Continued)

(56) References Cited

U.S. PATENT DOCUMENTS 7,700,643 B2  4/2010  Heeney et al.
8,343,636 B2  1/2013  Jen et al.
(Continued)

FOREIGN PATENT DOCUMENTS

GB  2424881 A  10/2006
GB  2525245 A  10/2015
(Continued)

OTHER PUBLICATIONS

Adam E. A. Contoret "Light-Emitting Fluorene Photoreactive Liquid Crystals for Organic Electroluminescence" Chem. Mater. 2004, 16, 4928-4936 (Year: 2004).*
(Continued)

*Primary Examiner* — Michael Y Sun
(74) *Attorney, Agent, or Firm* — Stinson LLP

(57) ABSTRACT

A compound of the formula, plus devices incorporating this compound, and a method of marking such devices:

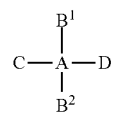

wherein:
A represents a phenyl group, a naphthyl group, a biphenyl group or two phenyl groups linked by a $C_1$-$C_8$ alkyl chain;

(Continued)

$B^1$ and $B^2$ in each occurrence are independently selected side chains of the structure —$(Y^1)_n$-L-$(Y^2)_m$—X wherein:
$Y^1$ and $Y^2$ in each occurrence are independently selected from O, $CO_2$— and $CH_2O$,
m and n in each occurrence are independently selected from 0 or 1;
L in each occurrence is a $C_2$-$C_{14}$ straight chain alkyl group; and
X in each occurrence is an independently selected cross linkable group;
C is a side chain of the structure —$(Z^1)_p$-M-$(Z^2)_q$-E
wherein:
$Z^1$ and $Z^2$ are independently selected from O, $CO_2$— and $CH_2O$,
p and q in each occurrence are independently selected from 0 or 1;
M is a $C_1$-$C_{14}$ straight chain alkyl group; and
E comprises a charge transport group;
D is a side chain of the structure —$(W^1)_r$—N—$(W^2)_s$—F
wherein:
$W^1$ and $W^2$ are independently selected from O, $CO_2$— and $CH_2O$,
r and s in each occurrence are independently selected from 0 or 1;
N is a $C_1$-$C_{14}$ straight chain alkyl group; and
F comprises a charge transport group or light emitter group;
and wherein the charge transport group E does not contain a fluorene group other than those that form part of a spirobifluorenearylamine motif.

18 Claims, 1 Drawing Sheet

(51) Int. Cl.

| | | |
|---|---|---|
| *C07D 207/452* | (2006.01) | |
| *C09K 11/06* | (2006.01) | |
| *C07C 217/80* | (2006.01) | |
| *C09K 19/20* | (2006.01) | |
| *C07C 215/74* | (2006.01) | |
| *C07C 219/34* | (2006.01) | |
| *C07C 69/92* | (2006.01) | |

(52) U.S. Cl.
CPC .......... *C09K 11/06* (2013.01); *H01L 51/0034* (2013.01); *H01L 51/0059* (2013.01); *H01L 51/0062* (2013.01); *H01L 51/5056* (2013.01); *C07C 69/92* (2013.01); *C07C 215/74* (2013.01); *C07C 219/34* (2013.01); *C09K 19/20* (2013.01); *C09K 2211/1416* (2013.01); *C09K 2211/1433* (2013.01); *H01L 51/0035* (2013.01); *H01L 51/0051* (2013.01); *Y02E 10/549* (2013.01)

(58) Field of Classification Search
CPC ............ H01L 51/0051; H01L 51/0035; C07D 207/452; Y02E 10/549; C07C 69/92; C07C 219/34; C07C 215/74; C07C 217/80; C09K 2211/1433; C09K 11/06; C09K 2211/1416; C09K 19/20
See application file for complete search history.

(56) References Cited

U.S. PATENT DOCUMENTS

| | | | |
|---|---|---|---|
| 9,252,366 B2 | 2/2016 | Hou | |
| 9,577,194 B2 | 2/2017 | Brown et al. | |
| 10,084,137 B2 | 9/2018 | Judd et al. | |
| 2002/0106531 A1 | 8/2002 | Naito | |
| 2005/0019602 A1* | 1/2005 | Sellinger | B82Y 20/00 428/690 |
| 2005/0031801 A1 | 2/2005 | Shundo et al. | |
| 2005/0089716 A1 | 4/2005 | Nakaya et al. | |
| 2005/0189873 A1 | 9/2005 | Kelly et al. | |
| 2006/0163562 A1 | 7/2006 | Boerner | |
| 2009/0184292 A1* | 7/2009 | Ohuchi | H01L 51/0039 252/301.35 |
| 2009/0295275 A1* | 12/2009 | Parham | H01L 51/0071 313/504 |
| 2010/0143612 A1 | 6/2010 | Hirai | |
| 2011/0105778 A1* | 5/2011 | Stoessel | C09B 57/10 556/406 |
| 2011/0133134 A1* | 6/2011 | Varma | C08L 33/02 252/511 |
| 2013/0324716 A1 | 12/2013 | Brown et al. | |
| 2017/0033290 A1 | 2/2017 | Judd et al. | |
| 2018/0019407 A1* | 1/2018 | Sakaino | H01L 31/10 |

FOREIGN PATENT DOCUMENTS

| | | | |
|---|---|---|---|
| JP | 2007163577 A | * | 6/2007 |
| JP | 2012168233 A | | 9/2012 |
| WO | 2005004251 A1 | | 1/2005 |
| WO | 2013173396 | | 11/2013 |
| WO | 2013173396 A2 | | 11/2013 |
| WO | 2015159098 A1 | | 10/2015 |

OTHER PUBLICATIONS

International Search Report and Written Opinion, PCT/GB2016/053171, dated Dec. 7, 2016, 10 pages.
Aldred et al., "Synthesis and mesomorphic behaviour of novel light-emitting liquid crystals," Liquid Crystals, 2005, vol. 32, Issue 10, pp. 1251-1264.
Kwon et al., "Nematic-like mesophase photoconductive polymer for photorefractive applications," Polymer, vol. 46, 2005, pp. 10301-10310.
Tang, Duofeng et al., "Research progress of crosslinkable electroluminescent polymers," GD Science & Technology, vol. 11, No. 225, 7 pages.
Bayerl Michael S et al., "Crosslinkable hole-transport materials for preparation of multilayer organic light emitting devices by spin-coating," Macromolecular Rapid Communications, 1999, vol. 20, No. 4, pp. 224-228.
Nuyken Oskar et al., "Crosslinkable hole- and electron-transport materials for application in organic light emitting devices(OLEDs)," Designed Monomers and Polymers, 2002, vol. 5, No. 2, pp. 195-210.

* cited by examiner

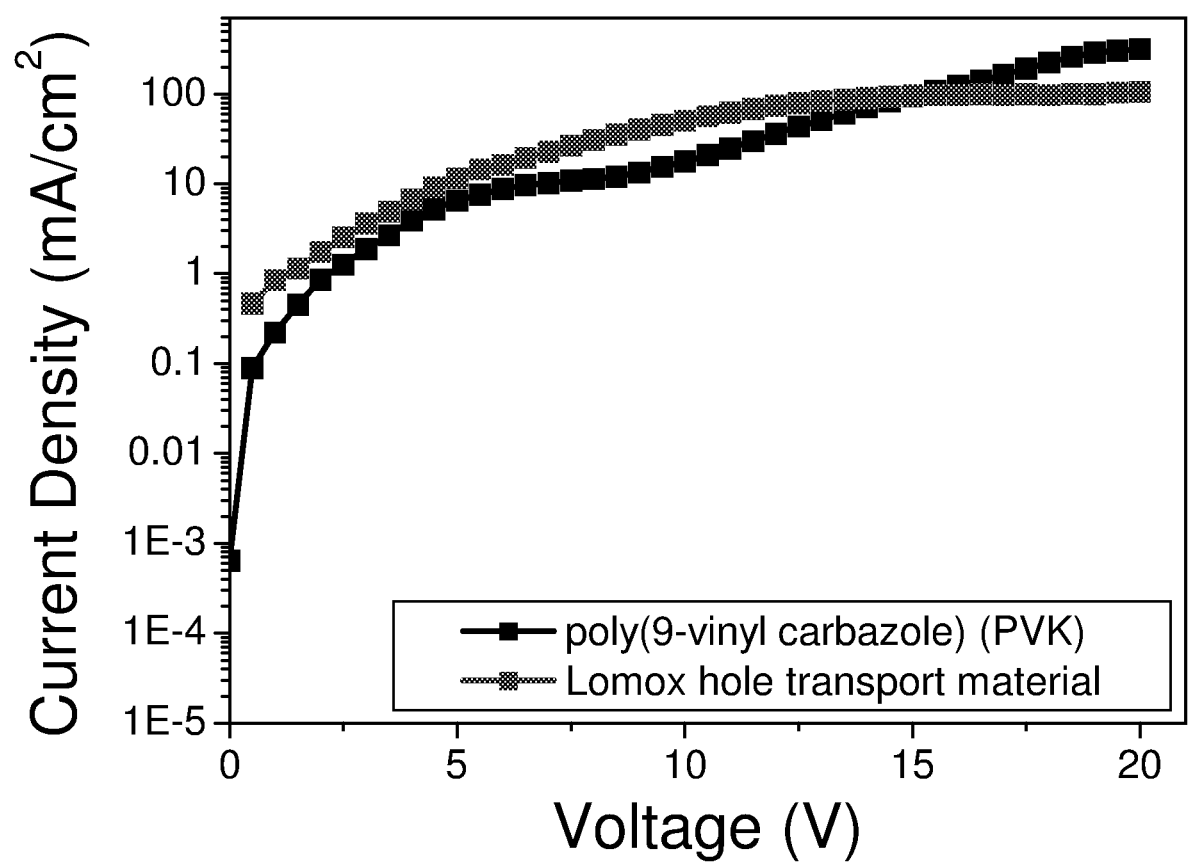

CROSS-LINKABLE CHARGE TRANSPORT MATERIALS

REFERENCE TO RELATED APPLICATIONS

This application is a U.S. national stage application of International Patent Application No. PCT/GB2016/053171, filed Oct. 13, 2016, and claims the benefit of priority of Great Britain Application No. 1518366.8, filed Oct. 16, 2015, the entire disclosures of which are incorporated herein by reference.

FIELD OF THE INVENTION

The present invention relates to novel cross-linkable compounds with charge transport properties that render them useful for the production of electrical devices. The invention further relates to electronic devices that incorporate layers comprising these compounds and methods for making such devices. The compounds of the invention function as charge transport materials that transport holes and electrons in electronic devices and can also function as hole injection layers. In addition in the case wherein the compounds of the invention contain charge transport motifs and photoluminescent motifs the compounds are useful for application as interface layers in, for example, organic light emitting diodes.

BACKGROUND OF THE INVENTION

Organic light emitting diodes (OLED) are light emitting diodes in which the emissive electroluminescent material is a film of organic material which emits light in response to an electrical current. The emissive organic layer of an OLED is sandwiched between two electrical contact layers. For enhanced efficiency, in addition to a light emitting layer, the OLED device may incorporate layers of charge transporting material between the emissive layer and the electrical contact layer. These charge transporting layers may comprise either hole transporting or electron transporting materials. These charge transport materials can allow the charge-carrying holes and electrons to migrate through to the emissive layer, thereby facilitating their combination to form a bound state called an exciton. The electrons in the excitons in due course relax into a lower energy state by emitting radiation which, for an OLED device, is of a frequency most often in the visible region.

Field-effect transistors (FET) are electronic devices that commonly operate as a capacitor. Field-effect transistors feature three essential components, namely a source, a drain and a gate. Structurally, FETs comprise two plates, one that serves as a conducting channel between two ohmic contacts that are called the source and the drain contacts. The other plate works to control the charge induced into the channel is called the gate. The direction of the movement of charge carriers in the channel is from the source to the drain. Hence the relationship between these three components is that the gate controls the carrier movement from the source to the drain. Organic field-effect transistors (OFET) are FETs that use an organic semi-conductor in their channel. Charge transport materials are therefore key components of OFETs and realisation of materials with optimised charge transport properties is an important aim. Materials that allow improved manufacturing processes such as patternable solution phase processing are also a significant target.

Organic photovoltaic materials and devices are also a subject of considerable interest due to the potential of this technology to generate power renewably and at low cost. Organic photovoltaic cells (OPVs) have attracted much interest as a possible alternative to the conventional, inorganic, photovoltaic technologies. OPVs are characteristically light in weight and flexible. They are also semi-transparent and are potentially cheaper to manufacture than conventional inorganic photovoltaic technologies because OPVs can be manufactured in a continuous process using state of the art printing tools. OPVs have great potential to revolutionise the field of solar cell technology.

There is considerable ongoing interest in the development of new materials with improved properties that are suitable for use in the fabrication of devices such as OLEDs, OPVs and OFETs. Materials that, for example, function as light emitters, electron transporters and hole transporters are of particular interest. Many materials have been developed over the years in the attempt to produce improved OLED devices and in particular devices with optimal light output, energy efficiency and life time. In addition, a further notable goal is the realisation of materials that allow the device fabrication process for OLEDs, OPVs and OFETs to be simplified. Notwithstanding existing materials, there is a continuing need for materials that have properties such as those identified above that possess superior combination of properties for the fabrication of OLEDs, OPVs, OFETs and other electronic devices.

It is known that some reactive mesogens (liquid crystalline materials capable of being chemically crosslinked into a polymer matrix) of the general formula:

where A represents a linear aromatic molecular core comprising a fluorene substituted with two alkyl groups at C-9, S represents flexible spacer units and B represents cross-linking groups such as methacrylate groups, may be useful in the fabrication of organic electronic devices. This is particularly the case if B represents a photo-crosslinkable group, since then the materials function essentially as photoresists, which is to say, thin layers of these materials may be patterned into useful electronic structures by patterned exposure to light, particularly UV light.

WO2005004251 relates to multifluorinated conductor materials for LEDs.

WO2015159098 relates to 2,7-disubstituted 9,9-fluoroalkyl fluorene derivatives.

Further, if the linear aromatic core A is luminescent in nature, these reactive mesogen materials may be patterned into the active light emitting layers in electroluminescent devices such as organic light emitting diodes (OLEDs) and organic diode lasers.

To construct an optimal OLED device from reactive mesogens such as those of the B-S-A-S-B structure and related structures there is a clear need for cross linkable materials that possess the necessary hole transport and charge transport properties to deliver optimal device performance and allow methods for device fabrication to be optimised. Materials with hole transport properties can also be used to form hole injection layers in OLEDs, OFETs and OPVs.

In order that a solution phase based device fabrication approach is practical the cross linkable materials must have adequate solubility in the solvent of choice, typical a hydrocarbon solvent such as benzene, toluene or xylene or halogenated derivatives thereof, and should also exhibit good film forming properties once dissolved in a solvent. A film is a layer of the relevant material dissolved in a solvent, for example a hydrocarbon solvent, that forms once a solution of the material is applied to the substrate and spreads on the surface of the substrate. Some or all of the solvent can then be removed by, for example, evaporation prior to cross linking by, for example, exposing the deposited layer to UV radiation. Achieving a uniform thickness of film on the substrate delivers a uniform distribution or thickness of the deposited layer of functional material on the substrate that can then be cross linked onto the substrate. Techniques such as spin coating can be used to assist uniform film formation. Film forming properties are therefore an important consideration for reproducible device layer production and, accordingly, OLEDs, OPVs and OFETs with reproducible performance characteristics.

In addition, cross linkable materials that have dual hole transport or charge transport properties in addition to luminescent properties that can serve as interface layers could further enhance the properties of OLEDs, OPVs and OFETs.

It is an object of the present invention to provide new cross linkable functional electronic materials for use in electronic device fabrication which overcome, or substantially reduce, problems associated with prior art charge transporting materials. It is also an object of the present invention to provide organic electronic devices, for example OLEDs, OPVs and OFETs featuring these materials and methods for their production.

SUMMARY OF THE INVENTION

In a first aspect of the present invention, there is provided a compound of Formula (I)

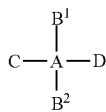

Formula (I)

wherein:

A represents a phenyl group, a naphthyl group, a biphenyl group or two phenyl groups linked by a $C_1$-$C_8$ alkyl chain;

$B^1$ and $B^2$ in each occurrence are independently selected side chains of the structure

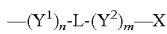

wherein:

$Y^1$ and $Y^2$ in each occurrence are independently selected from O, $CO_2$— and $CH_2O$, m and n in each occurrence are independently selected from 0 or 1;

L in each occurrence is a $C_2$-$C_{14}$ straight chain alkyl group; and

X in each occurrence is an independently selected cross linkable group;

C is a side chain of the structure

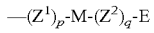

wherein:

$Z^1$ and $Z^2$ are independently selected from O, $CO_2$— and $CH_2O$, p and q in each occurrence are independently selected from 0 or 1;

M is a $C_1$-$C_{14}$ straight chain alkyl group; and

E comprises a charge transport group;

D is a side chain of the structure

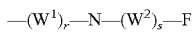

wherein:

$W^1$ and $W^2$ are independently selected from O, $CO_2$— and $CH_2O$, r and s in each occurrence are independently selected from 0 or 1;

N is a $C_1$-$C_{14}$ straight chain alkyl group; and

F comprises a charge transport group or light emitter group;

and wherein the charge transport group E does not contain a fluorene group other than those that form part of a spirobifluorenearylamine motif.

In one embodiment there is provided a compound of the formula Ia wherein A represents a phenyl or naphthyl group, further wherein $B^1$, $B^2$, C and D are as defined for compounds of formula I.

In one embodiment there is provided a compound of the formula Ib wherein A represents a biphenyl group, further wherein $B^1$, $B^2$, C and D are as defined for compounds of formula I.

In one embodiment there is provided a compound of the formula Ic wherein A represents two phenyl groups linked by a $C_1$-$C_8$ straight alkyl chain, further wherein $B^1$, $B^2$, C and D are as defined for compounds of formula I.

In one embodiment there is provided a compound of formula Id wherein A represents a two phenyl groups linked by a $C_1$-$C_8$ straight alkyl chain wherein the $B^1$ and C substituents are located on the first phenyl group and the $B^2$ and D substituents are located on the second phenyl group, further wherein $B^1$, $B^2$, C and D are as defined for compounds of formula I.

In one embodiment there is provided a compound of the formula Ie wherein A represents a phenyl group, further wherein $B^1$, $B^2$, C and D are as defined for compounds of formula I.

In one embodiment there is provided a compound of the formula If wherein A represents a 1,2,4,5-substituted phenyl group, further wherein $B^1$, $B^2$, C and D are as defined for compounds of formula I.

In one embodiment there is provided a compound of the formula Ig wherein A represents a 1,2,4,5-substituted phenyl group and groups C and D are para- to each other, further wherein $B^1$, $B^2$, C and D are as defined for compounds of formula I.

In one embodiment there is provided a compound of formula Ih wherein the group X of $B^1$ or $B^2$ is in each case selected from the group comprising alkene cross linking groups, thiols and oxetane, further wherein A, C, D and the other components of $B^1$ and $B^2$ are as defined for compounds of formula (I), (Ia), (Ib), (Ic), (Id), (Ie), (If) and (Ig).

In one embodiment there is provided a compound of formula Ii wherein the group X of $B^1$ or $B^2$ is in each case selected from the group comprising electron rich or electron poor alkene cross linking groups, further wherein A, C, D and the other components of $B^1$ and $B^2$ are as defined for compounds of formula (I), (Ia), (Ib), (Ic), (Id), (Ie), (If) and (Ig).

In one embodiment there is provided a compound of formula Ij wherein the group X of $B^1$ or $B^2$ is in each case selected from the group comprising photopolymerisable alkene cross linking groups, further wherein A, C, D and the other components of $B^1$ and $B^2$ are as defined for compounds formula (I), (Ia), (Ib), (Ic), (Id), (Ie), (If) and (Ig).

In one embodiment there is provided a compound of formula Ik wherein the group X of $B^1$ or $B^2$ is in each case selected from the group consisting of straight chain and cyclic $\alpha,\beta$-unsaturated esters, $\alpha,\beta$-unsaturated amides and vinyl ethers, further wherein A, C, D and the other components of $B^1$ and $B^2$ are as defined for compounds of formula (I), (Ia), (Ib), (Ic), (Id), (Ie), (If) and (Ig).

In one embodiment there is provided a compound of formula IL wherein the group X of $B^1$ or $B^2$ is in each case selected from the group consisting of methacrylate, ethacrylate, ethylmaleato, ethylfumarato, N-maleimido, vinyloxy, alkylvinyloxy, vinylmaleato, vinylfumarato and N-(2-vinyloxymaleimido) groups, further wherein A, C, D and the other components of $B^1$ and $B^2$ are as defined for compounds of formula (I), (Ia), (Ib), (Ic), (Id), (Ie), (If) and (Ig).

In one embodiment there is provided a compound of formula Im wherein the group L of $B^1$ or $B^2$ is in each case selected from $C_4$ to $C_{10}$ alkyl groups, further wherein A, C, D and the other components of $B^1$ and $B^2$ are as defined for compounds of formula (I), (Ia), (Ib), (Ic), (Id), (Ie), (If) and (Ig).

In one embodiment there is provided a compound of formula In wherein the group L of $B^1$ or $B^2$ is in each case selected from $C_4$ to $C_8$ alkyl groups, further wherein A, C, D and the other components of $B^1$ and $B^2$ are as defined for compounds of formula (I), (Ia), (Ib), (Ic), (Id), (Ie), (If), (Ig), (Ih), (Ii), (Ij), (Ik), (IL) and (Im).

In one embodiment there is provided a compound of formula Io wherein the integers m and n are 1, further wherein A, C, D and the other components of $B^1$ and $B^2$ are as defined for compounds of formula (I), (Ia), (Ib), (Ic), (Id), (Ie), (If), (Ig), (Ih), (Ii), (Ij), (Ik), (IL), (Im) and (In).

In one embodiment there is provided a compound of formula Ip wherein the group $Y^1$ in both $B^1$ and $B^2$ is an oxygen atom, further wherein A, C, D and the other components of $B^1$ and $B^2$ are as defined for compounds of formula (I), (Ia), (Ib), (Ic), (Id), (Ie), (If), (Ig), (Ih), (Ii), (Ij), (Ik) (Im), (In) and (Io).

In one embodiment there is provided a compound of formula Iq wherein the group $Y^1$ in both $B^1$ and $B^2$ are $CO_2$, i.e. an ester linkage, further wherein A, C, D and the other components of $B^1$ and $B^2$ are as defined for compounds of formula (I), (Ia), (Ib), (Ic), (Id), (Ie), (If), (Ig), (Ih), (Ii), (Ij), (Ik) (Im), (In) and (Io).

In one embodiment there is provided a compound of formula Ir wherein the groups $Z^1$ of C and $W^1$ of D are in each case an oxygen atom, further wherein A, $B^1$, $B^2$, D and the other components of C are as defined for compounds of formula (I), (Ia), (Ib), (Ic), (Id), (Ie), (If), (Ig), (Ih), (Ii), (Ij), (Ik) (Im), (In), (Io), (Ip) and (Iq).

In one embodiment there is provided a compound of formula Is wherein the groups $Z^1$ of C and $W^1$ of D are in each case $CO_2$, i.e. an ester linkage, further wherein A, $B^1$, $B^2$, C and the other components of D are as defined for compounds of formula (I), (Ia), (Ib), (Ic), (Id), (Ie), (If), (Ig), (Ih), (Ii), (Ij), (Ik) (Im), (In), (Io), (Ip) and (Iq).

In one embodiment there is provided a compound of formula It wherein the groups M of C and N of D, respectively, are $C_4$ to $C_{12}$ alkyl groups, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir) and (Is).

In one embodiment there is provided a compound of formula Iu wherein the groups M of C and N of D, respectively, are $C_6$ alkyl groups, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir) and (Is).

In one embodiment there is provided a compound of formula Iv wherein the integers p and r are both 1, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir), (Is), (It) and (Iu).

In one embodiment there is provided a compound of formula Iw wherein integers p and r are both 0, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir), (Is), (It) and (Iu).

In one embodiment there is provided a compound of formula Ix wherein integers q and s are both 1, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir), (Is), (It), (Iu), (Iv) and (Iw).

In one embodiment there is provided a compound of formula Iy wherein integers p and r are both 0, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir), (Is), (It), (Iu), (Iv), (Iw) and (Ix).

In one embodiment there is provided a compound of formula Iz wherein the groups $Z^1$ of C and $W^1$ of D are oxygen atoms, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir), (Is), (It), (Iu), (Iv), (Iw), (Ix) and (Iy).

In one embodiment there is provided a compound of formula Iaa wherein the groups E and F comprise a hole transport group, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir), (Is), (It), (Iu), (Iv), (Iw), (Ix), (Iy) and (Iz).

In one embodiment there is provided a compound of formula Iab wherein the groups E and F comprise an electron transport group, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir), (Is), (It), (Iu), (Iv), (Iw), (Ix), (Iy) and (Iz).

In one embodiment there is provided a compound of formula Iac wherein the group E is a hole transport group and the group F is an electron transport group, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir), (Is), (It), (Iu), (Iv), (Iw), (Ix), (Iy) and (Iz).

In one embodiment there is provided a compound of formula Iad wherein the group E and/or F is a hole transporting group that comprises a triarylamine hole transport motif or a carbazole hole transport motif, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir), (Is), (It), (Iu), (Iv), (Iw), (Ix), (Iy) and (Iz).

In one embodiment there is provided a compound of formula Iae wherein the group E and/or F is a hole transporting group that comprises a triaryl amine, such as a triphenylamine or a spirobifluorenearylamine, a 3,6-carbazole, a, 2,7-carbazole, a 1,3,6,8-carbazole, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir), (Is), (It), (Iu), (Iv), (Iw), (Ix), (Iy) and (Iz).

In one embodiment there is provided a compound of formula Iaf wherein the group E and/or F is hole transporting group that comprises a straight or branched chain containing between one and ten, between one and six or between three and six hole transport motifs selected from triarylamine, such as a triphenylamine or a spirobifluorenearylamine, a 3,6-carbazole, a, 2,7-carbazole, a 1,3,6,8-carbazole or a spirobifluorenearylamine, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir), (Is), (It), (Iu), (Iv), (Iw), (Ix), (Iy) and (Iz).

In one embodiment there is provided a compound of formula Iag wherein the group E and/or F is hole transporting group that can be described by the general formula

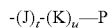

wherein J is a phenyl group, a benzyl group, a biphenyl group, a 2,2'-bithiophene group, a fused thiophene group or thiophene, t is 0 or 1, K is a hole transporting motif selected from triarylamine, such as a triphenylamine or a spirobifluorenearylamine, 3,6-carbazole, 2,7-carbazole or 1,3,6,8-carbazole linked to adjacent members of the chain via a covalent bond, a phenyl group, a fused thiophene group or thiophene, u is an integer from 1 to 10, for example from 1 to 6 or from 3 to 6, and P is a chain terminating group selected from hydrogen, $C_1$-$C_8$ straight or branched alkyl, phenyl, $C_1$-$C_8$ straight or branched alkyl substituted phenyl, or $C_1$-$C_8$ straight or branched alkyl substituted biphenyl, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir), (Is), (It), (Iu), (Iv), (Iw), (Ix), (Iy) and (Iz).

In one embodiment there is provided a compound of formula Iah wherein the group E and/or F is hole transporting group that can be described by the general formula

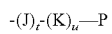

wherein J is a phenyl group, a benzyl group, a biphenyl group, a 2,2'-bithiophene group, a fused thiophene group or thiophene, t is 0 or 1, K is a hole transporting motif selected from triarylamine, such as a triphenylamine or a spirobifluorenearylamine, 3,6-carbazole, 2,7-carbazole or 1,3,6,8-carbazole linked to adjacent members of the chain via a covalent bond, a phenyl group, a fused thiophene group or thiophene, u is an integer from 1 to 6, and P is a chain terminating group selected from hydrogen, $C_1$-$C_8$ straight or branched alkyl, phenyl, $C_1$-$C_8$ straight or branched alkyl substituted phenyl, or $C_1$-$C_8$ straight or branched alkyl substituted biphenyl, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir), (Is), (It), (Iu), (Iv), (Iw), (Ix), (Iy) and (Iz).

In one embodiment there is provided a compound of formula Iai wherein the group E and/or F is hole transporting group that can be described by the general formula

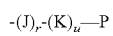

wherein J is a phenyl group, a benzyl group, a biphenyl group, a 2,2'-bithiophene group, a fused thiophene group or thiophene, t is 0 or 1, K is a hole transporting motif selected from triarylamine, such as a triphenylamine or a spirobifluorenearylamine, 3,6-carbazole, 2,7-carbazole or 1,3,6,8-carbazole linked to adjacent members of the chain via a covalent bond, a phenyl group, a fused thiophene group or thiophene, u is an integer from 3 to 6, and P is a chain terminating group selected from hydrogen, $C_1$-$C_8$ straight or branched alkyl, phenyl, $C_1$-$C_8$ straight or branched alkyl substituted phenyl, or $C_1$-$C_8$ straight or branched alkyl substituted biphenyl, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir), (Is), (It), (Iu), (Iv), (Iw), (Ix), (Iy) and (Iz).

In one embodiment there is provided a compound of formula Iaj wherein the group E and/or F is an electron transporting group that comprises an electron transporting motif selected from benzimidazole, oxadiazole, triazole, phenanthroline, 2-phenylpyridine, 1,3,5-triazine, thiadiazole or (8-hydroxylquinoline) aluminium, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir), (Is), (It), (Iu), (Iv), (Iw), (Ix), (Iy) and (Iz).

In one embodiment there is provided a compound of formula Iak wherein the group E and/or F is an electron transporting group that contains an electron transporting motif selected from benzimidazole, oxadiazole, triazole, phenanthroline, 2-phenylpyridine, 1,3,5-triazine, thiadiazole or (8-hydroxylquinoline)aluminium linked to the other components of C or D as appropriate via a covalent bond, a phenyl group or a biphenyl group, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir), (Is), (It), (Iu), (Iv), (Iw), (Ix), (Iy) and (Iz).

In one embodiment there is provided a compound of formula IaL wherein the group E and/or F is an electron transporting group that comprises an electron transport motif that comprises benzimidazole, oxadiazole, triazole, phenanthroline, 2-phenylpyrimidine, 1,3,5-triazine, thiadiazole or (8-hydroxylquinoline)aluminium and at the terminus of the group E or F respectively i) a $C_1$-$C_8$ alkyl group, ii) an optionally substituted phenyl group or iii) an optionally substituted biphenyl group, wherein the optional substituent is a $C_1$-$C_8$ alkyl group, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir), (Is), (It), (Iu), (Iv), (Iw), (Ix), (Iy) and (Iz).

In one embodiment there is provided a compound of formula Iam wherein the group E and/or F is an electron transporting group that comprises an electron transporting motif selected from benzimidazole, oxadiazole, triazole, phenanthroline, 2-phenylpyrimidine, 1,3,5-triazine, thiadiazole or (8-hydroxylquinoline)aluminium linked to the other components of C or D as appropriate via a covalent bond, a phenyl group or a biphenyl group, and at the terminus of the group E or F respectively i) a $C_1$-$C_8$ alkyl group, ii) an optionally substituted phenyl group or iii) an optionally substituted biphenyl group, wherein the optional substituent is a $C_1$-$C_8$ alkyl group, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir), (Is), (It), (Iu), (Iv), (Iw), (Ix), (Iy) and (Iz).

In one embodiment there is provided a compound of formula Ian wherein the group E and/or F is an electron transporting group that comprises a chain comprising from one to ten, from one to six or from three to six electron transporting motifs selected from benzimidazole, oxadiazole, triazole, phenanthroline, 2-phenylpyrimidine, 1,3,5-triazine or thiadiazole mutually connected by covalent bonds, phenyl, methylene or $C_1$-$C_5$ heterocycle linkages, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir), (Is), (It), (Iu), (Iv), (Iw), (Ix), (Iy) and (Iz).

In one embodiment there is provided a compound of formula Iao wherein the group E and/or F is an electron transporting group that comprises a chain comprising from one to ten, from one to six or from three to six electron transporting motifs selected from benzimidazole, oxadiazole, triazole, phenanthroline, 2-phenylpyrimidine, 1,3,5-triazine or thiadiazole mutually connected by covalent bonds, phenyl or $C_1$-$C_5$ heterocycle linkages, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir), (Is), (It), (Iu), (Iv), (Iw), (Ix), (Iy) and (Iz).

In one embodiment there is provided a compound of formula Iap wherein the group E and/or F is an electron transporting group that comprises a chain comprising from one to ten, from one to six or from three to six electron transporting motifs selected from benzimidazole, oxadiazole, triazole, phenanthroline, 2-phenylpyrimidine, 1,3,5-triazine or thiadiazole mutually connected by covalent bonds, phenyl or $C_1$-$C_5$ heterocycle linkages and linked to the other components of C or D, as appropriate, via a covalent bond, a phenyl group or a biphenyl group, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir), (Is), (It), (Iu), (Iv), (Iw), (Ix), (Iy) and (Iz).

In one embodiment there is provided a compound of formula Iaq wherein the group E and/or F is an electron transporting group that comprises a chain comprising from one to ten, from one to six or from three to six electron transporting motifs selected from benzimidazole, oxadiazole, triazole, phenanthroline, 2-phenylpyrimidine, 1,3,5-triazine or thiadiazole mutually connected by covalent bonds, phenyl or $C_1$-$C_5$ heterocycle linkages, and at the terminus of the group E or F, respectively, i) a $C_1$-$C_8$ alkyl group, ii) an optionally substituted phenyl group or iii) an optionally substituted biphenyl group, wherein the optional substituent is a $C_1$-$C_8$ alkyl group, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir), (Is), (It), (Iu), (Iv), (Iw), (Ix), (Iy) and (Iz).

In one embodiment there is provided a compound of formula Iar wherein the group E and/or F is an electron transporting group that comprises a chain comprising from one to six electron transporting motifs selected from benzimidazole, oxadiazole, triazole, phenanthroline, 2-phenylpyrimidine, 1,3,5-triazine or thiadiazole mutually connected by covalent bonds, phenyl, methylene or $C_1$-$C_5$ heterocycle linkages and linked to the other components of C or D as appropriate via a covalent bond, a phenyl group or a biphenyl group, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir), (Is), (It), (Iu), (Iv), (Iw), (Ix), (Iy) and (Iz).

In one embodiment there is provided a compound of formula Ias wherein the group E and/or F is an electron transporting group that comprises a chain comprising from one to six electron transporting motifs selected from benzimidazole, oxadiazole, triazole, phenanthroline, 2-phenylpyrimidine, 1,3,5-triazine or thiadiazole mutually connected by covalent bonds or phenyl linkages and linked to the other components of C or D as appropriate via a covalent bond, a phenyl group or a biphenyl group, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir), (Is), (It), (Iu), (Iv), (Iw), (Ix), (Iy) and (Iz).

In one embodiment there is provided a compound of formula Iat wherein the group E and/or F is an electron transporting group that comprises a chain comprising from one to six electron transporting motifs selected from benzimidazole, oxadiazole, triazole, phenanthroline, 2-phenylpyrimidine, 1,3,5-triazine or thiadiazole mutually connected by covalent bonds, phenyl or $C_1$-$C_5$ heterocycle linkages and linked to the other components of C or D as appropriate via a covalent bond, a phenyl group or a biphenyl group, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir), (Is), (It), (Iu), (Iv), (Iw), (Ix), (Iy) and (Iz).

In one embodiment there is provided a compound of formula Iau wherein the group E and/or F is an electron transporting group that comprises a chain comprising from one to six electron transporting motifs selected from benzimidazole, oxadiazole, triazole, phenanthroline, 2-phenylpyrimidine, 1,3,5-triazine or thiadiazole mutually connected by covalent bonds, phenyl or $C_1$-$C_5$ heterocycle linkages, and at the terminus of the group E or F respectively i) a $C_1$-$C_8$ alkyl group, ii) an optionally substituted phenyl group or iii) an optionally substituted biphenyl group, wherein the optional substituent is a $C_1$-$C_8$ alkyl group and wherein each chain is optionally linked to the other components of C or D as appropriate via a phenyl or biphenyl group, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir), (Is), (It), (Iu), (Iv), (Iw), (Ix), (Iy) and (Iz).

In one embodiment there is provided a compound of formula Iav wherein the group E and/or F is an electron transporting group that comprises a chain comprising from three to six electron transporting motifs selected from benzimidazole, oxadiazole, triazole, phenanthroline, 2-phenylpyrimidine, 1,3,5-triazine or thiadiazole mutually connected by covalent bonds, phenyl or $C_1$-$C_5$ heterocycle linkages, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir), (Is), (It), (Iu), (Iv), (Iw), (Ix), (Iy) and (Iz).

In one embodiment there is provided a compound of formula Iaw wherein the group E and/or F is an electron transporting group that comprises a chain comprising from three to six electron transporting motifs selected from benzimidazole, oxadiazole, triazole, phenanthroline, 2-phenylpyrimidine, 1,3,5-triazine or thiadiazole mutually connected by covalent bonds, phenyl or $C_1$-$C_5$ heterocycle linkages, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir), (Is), (It), (Iu), (Iv), (Iw), (Ix), (Iy) and (Iz).

In one embodiment there is provided a compound of formula Iax wherein the group E and/or F is an electron transporting group that comprises a chain comprising from three to six electron transporting motifs selected from benzimidazole, oxadiazole, triazole, phenanthroline, 2-phenylpyrimidine, 1,3,5-triazine or thiadiazole mutually connected by covalent bonds, phenyl or $C_1$-$C_5$ heterocycle linkages and linked to the other components of C or D as appropriate via a covalent bond, a phenyl group or a biphenyl group, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir), (Is), (It), (Iu), (Iv), (Iw), (Ix), (Iy) and (Iz).

In one embodiment there is provided a compound of formula Iay wherein the group E and/or F is an electron transporting group that comprises a chain comprising from three to six electron transporting motifs selected from benzimidazole, oxadiazole, triazole, phenanthroline, 2-phenylpyrimidine, 1,3,5-triazine or thiadiazole mutually connected by covalent bonds, phenyl or $C_1$-$C_5$ heterocycle linkages and linked to the other components of C or D as appropriate via a covalent bond, a phenyl group or a biphenyl group, and at the terminus of the group E or F respectively i) a $C_1$-$C_8$ alkyl group, ii) an optionally substituted phenyl group or iii) an optionally substituted biphenyl group, wherein the optional substituent is a $C_1$-$C_8$ alkyl group, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir), (Is), (It), (Iu), (Iv), (Iw), (Ix), (Iy) and (Iz).

In one embodiment there is provided a compound of formula Iaz wherein the group E and/or F is an electron transporting group that is an electron transporting motif selected from benzimidazole, oxadiazole, triazole, phenanthroline, 2-phenylpyrimidine, 1,3,5-triazine, thiadiazole or (8-hydroxylquinoline)aluminium, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir), (Is), (It), (Iu), (Iv), (Iw), (Ix), (Iy) and (Iz).

In one embodiment there is provided a compound of formula Iba wherein the group E and/or F is an electron transporting group that comprises an electron transporting motif selected from benzimidazole, oxadiazole, triazole, phenanthroline, 2-phenylpyrimidine, 1,3,5-triazine, thiadiazole or (8-hydroxylquinoline)aluminium linked to the other components of C or D as appropriate via a covalent bond, a phenyl group or a biphenyl group, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir), (Is), (It), (Iu), (Iv), (Iw), (Ix), (Iy) and (Iz).

In one embodiment there is provided a compound of formula Ibb wherein the group E and/or F is an electron transporting group that comprises an electron transporting motif selected from benzimidazole, oxadiazole, triazole, phenanthroline, 2-phenylpyrimidine, 1,3,5-triazine, thiadiazole or (8-hydroxylquinoline)aluminium that terminates in i) a $C_1$-$C_8$ alkyl group, ii) an optionally substituted phenyl group or iii) an optionally substituted biphenyl group, wherein the optional substituent is a $C_1$-$C_8$ alkyl group, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir), (Is), (It), (Iu), (Iv), (Iw), (Ix), (Iy) and (Iz).

In one embodiment there is provided a compound of formula Ibc wherein the group E and/or F is an electron transporting group that comprises an electron transporting motif selected from benzimidazole, oxadiazole, triazole, phenanthroline, 2-phenylpyrimidine, 1,3,5-triazine, thiadiazole or (8-hydroxylquinoline)aluminium linked to the other components of C or D as appropriate via a covalent bond, a phenyl group or a biphenyl group and that terminates in i) a $C_1$-$C_8$ alkyl group, ii) an optionally substituted phenyl group or iii) an optionally substituted biphenyl group, wherein the optional substituent is a $C_1$-$C_8$ alkyl group, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik) (Im), (In), (Io), (Ip), (Iq), (Ir), (Is), (It), (Iu), (Iv), (Iw), (Ix), (Iy) and (Iz).

In one embodiment there is provided a compound of formula (Iad), (Iae), (Iaf), (Iag), (Iah) or (Iai) wherein the groups E and F are hole transporting groups.

In one embodiment there is provided a compound of formula (Iaj), (Iak), (Iam), (Ian), (Iao), (Iap), (Iaq), (Iar), (Ias), (Iat), (Iau), (Iay), (Iaw), (Iax), (Iay), (Iaz), (Iba), (Ibb) or (Ibc) wherein the groups E and F are hole transporting groups.

In one embodiment there is provided a compound of formula (Iad), (Iae), (Iaf), (Iag), (Iah) or (Iai) wherein the group F is a light emitting group.

In one embodiment there is provided a compound of formula (Iaj), (Iak), (Iam), (Ian), (Iao), (Iap), (Iaq), (Iar), (Ias), (Iat), (Iau), (Iay), (Iaw), (Iax), (Iay), (Iaz), (Iba), (Ibb) or (Ibc) wherein the group F is a light emitting group.

In one embodiment there is provided a compound of formula (Ibd) wherein the group F is a light emitting group comprising a group FL of the structure

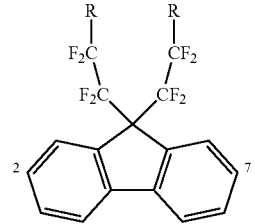

wherein the R groups of each FL moiety are identical and are selected from the group consisting of straight chain or branched achiral $C_1$-$C_{14}$ alkyl, $C_1$-$C_{14}$ haloalkyl, $C_1$-$C_{14}$ fluoroalkyl, $C_2$-$C_{14}$ alkenyl group, optionally wherein 1, 2, 3, 4 or 5 $CH_2$ groups are replaced by an oxygen provided that no acetal, ketal, peroxide or vinyl ether is present in the R group, further wherein A, $B^1$, $B^2$ and the other components of C and D are as defined for compounds of formula (I), (Ia), (Ib), (Ic), (Id), (Ie), (If), (Ig), (Ih), (Ii), (ID, (Ik), (Im), (In), (Io), (Ip), (Iq), (Ir), (Is), (It), (Iu), (Iv), (Iw), (Ix), (Iy), (Iz), (Iad), (Iae), (Iaf), (Iag), (Iah), (Iai), (Iaj), (Iak) (Iam), (Ian), (Iao), (Iap), (Iaq), (Iar), (Ias), (Iat), (Iau), (Iay), (Iaw), (Iax), (Iay), (Iaz), (Iba), (Ibb) or (Ibc).

In one embodiment there is provided a compound of formula (Ibe) wherein the group F is a light emitting group comprising a group FL of the structure

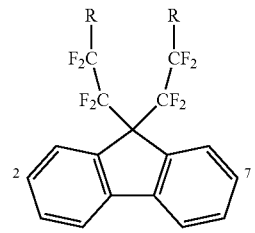

wherein the R groups of each FL moiety are identical and are selected from the group consisting of straight chain or branched achiral $C_1$-$C_{14}$ alkyl, further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik), (Im), (In), (Io), (Ip), (Iq), (Ir), (Is), (It), (Iu), (Iy), (Iw), (Ix), (Iy), (Iz), (Iad), (Iae), (Iaf), (Iag), (Iah), (Iai), (Iaj), (Iak) (Iam), (Ian), (Iao), (Iap), (Iaq), (Iar), (Ias), (Iat), (Iau), (Iay), (Iaw), (Iax), (Iay), (Iaz), (Iba), (Ibb) or (Ibc).

In one embodiment there is provided a compound of formula (Ibf) wherein the group F is a light emitting group of the structure

that comprises from 1 to 8 FL groups and wherein the dash at the left hand side of the formula indicates the site of connection to the other components of the group F;

wherein $Ar^1$ and $Ar^2$ in each occurrence are independently selected from the group comprising $Ar^a$ and a bond;

$Ar^a$ represents a diradical comprising 1 aromatic, heteroaromatic or FL moiety, or 2, 3, 4 or 5 aromatic, heteroaromatic and/or FL moieties mutually connected by a single bond;

n is an integer from 1 to 8;

Q is a hydrogen, $C_1$-$C_{14}$ alkyl, $C_1$-$C_{14}$ haloalkyl or $C_1$-$C_{14}$ fluoroalkyl group;

FL is a fluorene moiety of the structure

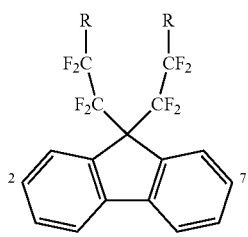

incorporated into the chain through covalent bonds at C-2 and C-7;

the R groups of each FL moiety are identical and are selected from the group consisting of straight chain or branched achiral $C_1$-$C_{14}$ alkyl, $C_1$-$C_{14}$ haloalkyl, $C_1$-$C_{14}$ fluoroalkyl, $C_2$-$C_{14}$ alkenyl group, optionally wherein 1, 2, 3, 4 or 5 $CH_2$ groups are replaced by an oxygen provided that no acetal, ketal, peroxide or vinyl ether is present in the R group;

further wherein A, $B^1$, $B^2$ and the other components of C and D are as defined for compounds of formula (I), (Ia), (Ib), (Ic), (Id), (Ie), (If), (Ig), (Ih), (Ii), (Ij), (Ik), (Im), (In), (Io), (Ip), (Iq), (Ir), (Is), (It), (Iu), (Iv), (Iw), (Ix), (Iy), (Iz), (Iad), (Iae), (Iaf), (Iag), (Iah), (Iai), (Iaj), (Iak) (Iam), (Ian), (Iao), (Iap), (Iaq), (Iar), (Ias), (Iat), (Iau), (Iay), (Iaw), (Iax), (Iay), (Iaz), (Iba), (Ibb) or (Ibc).

In one embodiment there is provided a network polymer formed by crosslinking a plurality of monomers of the formula (I), (Ia), (Ib), (Ic), (Id), (Ie), (If), (Ig), (Ih), (Ii), (Ij), (Ik), (Im), (In), (Io), (Ip), (Iq), (Ir), (Is), (It), (Iu), (Iv), (Ivy), (Ix), (Iy), (Iz), (Iad), (Iae), (Iaf), (Iag), (Iah), (Iai), (Iaj), (Iak) (Iam), (Ian), (Iao), (Iap), (Iaq), (Iar), (Ias), (Iat), (Iau), (Iay), (Iaw), (Iax), (Iay), (Iaz), (Iba), (Ibb), (Ibc), (Ibd), (Ibe) or (Ibf).

In one embodiment there is provided a compound with a structure of the formula (I), (Ia), (Ib), (Ic), (Id), (Ie), (If), (Ig), (Ih), (Ii), (Ij), (Ik), (Im), (In), (Io), (Ip), (Iq), (Ir), (Is), (It), (Iu), (Iv), (Iw), (Ix), (Iy), (Iz), (Iad), (Iae), (Iaf), (Iag), (Iah), (Iai), (Iaj), (Iak) (Iam), (Ian), (Iao), (Iap), (Iaq), (Iar), (Ias), (Iat), (Iau), (Iay), (Iaw), (Iax), (Iay), (Iaz), (Iba), (Ibb), (Ibc), (Ibd), (Ibe) or (Ibf) for use in the fabrication of an OLED device.

In one embodiment there is provided a compound with a structure of the formula (I), (Ia), (Ib), (Ic), (Id), (Ie), (If), (Ig), (Ih), (Ii), (Ij), (Ik), (Im), (In), (Io), (Ip), (Iq), (Ir), (Is), (It), (Iu), (Iv), (Iw), (Ix), (Iy), (Iz), (Iad), (Iae), (Iaf), (Iag), (Iah), (Iai), (Iaj), (Iak) (Iam), (Ian), (Iao), (Iap), (Iaq), (Iar), (Ias), (Iat), (Iau), (Iay), (Iaw), (Iax), (Iay), (Iaz), (Iba), (Ibb), (Ibc), (Ibd), (Ibe) or (Ibf) for use in the fabrication of an OFET device.

In one embodiment there is provided a compound with a structure of the formula (I), (Ia), (Ib), (Ic), (Id), (Ie), (If), (Ig), (Ih), (Ii), (Ij), (Ik), (Im), (In), (Io), (Ip), (Iq), (Ir), (Is), (It), (Iu), (Iv), (Iw), (Ix), (Iy), (Iz), (Iad), (Iae), (Iaf), (Iag), (Iah), (Iai), (Iaj), (Iak) (Iam), (Ian), (Iao), (Iap), (Iaq), (Iar), (Ias), (Iat), (Iau), (Iay), (Iaw), (Iax), (Iay), (Iaz), (Iba), (Ibb), (Ibc), (Ibd), (Ibe) or (Ibf) for use in the fabrication of an OPV device.

In one embodiment there is provided an OLED device comprising a compound of the formula (I), (Ia), (Ib), (Ic), (Id), (Ie), (If), (Ig), (Ih), (Ii), (Ij), (Ik), (Im), (In), (Io), (Ip), (Iq), (Ir), (Is), (It), (Iu), (Iv), (Iw), (Ix), (Iy), (Iz), (Iad), (Iae), (Iaf), (Iag), (Iah), (Iai), (Iaj), (Iak) (Iam), (Ian), (Iao), (Iap), (Iaq), (Iar), (Ias), (Iat), (Iau), (Iay), (Iaw), (Iax), (Iay), (Iaz), (Iba), (Ibb), (Ibc), (Ibd), (Ibe) or (Ibf) or a cross linked derivative thereof.

In one embodiment there is provided an OFET device comprising a compound of the formula (I), (Ia), (Ib), (Ic), (Id), (Ie), (If), (Ig), (Ih), (Ii), (Ij), (Ik), (Im), (In), (Io), (Ip), (Iq), (Ir), (Is), (It), (Iu), (Iv), (Iw), (Ix), (Iy), (Iz), (Iad), (Iae), (Iaf), (Iag), (Iah), (Iai), (Iaj), (Iak) (Iam), (Ian), (Iao), (Iap), (Iaq), (Iar), (Ias), (Iat), (Iau), (Iay), (Iaw), (Iax), (Iay), (Iaz), (Iba), (Ibb), (Ibc), (Ibd), (Ibe) or (Ibf) or a cross linked derivative thereof.

In one embodiment there is provided an OPV device comprising a compound of the formula (I), (Ia), (Ib), (Ic), (Id), (Ie), (If), (Ig), (Ih), (Ii), (Ij), (Ik), (Im), (In), (Io), (Ip), (Iq), (Ir), (Is), (It), (Iu), (Iv), (Iw), (Ix), (Iy), (Iz), (Iad), (Iae), (Iaf), (Iag), (Iah), (Iai), (Iaj), (Iak) (Iam), (Ian), (Iao), (Iap), (Iaq), (Iar), (Ias), (Iat), (Iau), (Iay), (Iaw), (Iax), (Iay), (Iaz), (Iba), (Ibb), (Ibc), (Ibd), (Ibe) or (Ibf) or a cross linked derivative thereof.

In one embodiment here is provided a device containing a charge transport layer containing a compound of the formula (I), (Ia), (Ib), (Ic), (Id), (Ie), (If), (Ig), (Ih), (Ii), (Ij), (Ik), (Im), (In), (Io), (Ip), (Iq), (Ir), (Is), (It), (Iu), (Iv), (Iw), (Ix), (Iy), (Iz), (Iad), (Iae), (Iaf), (Iag), (Iah), (Iai), (Iaj), (Iak) (Iam), (Ian), (Iao), (Iap), (Iaq), (Iar), (Ias), (Iat), (Iau), (Iay), (Iaw), (Iax), (Iay), (Iaz), (Iba), (Ibb), (Ibc), (Ibd), (Ibe) or (Ibf) or a cross linked derivative thereof.

In one embodiment here is provided a device containing a hole injection layer containing a compound of the formula (Iaa) or a cross linked derivative thereof.

In one embodiment here is provided a photovoltaic device or thin film transistor containing a charge transport layer containing a compound of the formula (I), (Ia), (Ib), (Ic), (Id), (Ie), (If), (Ig), (Ih), (Ii), (Ij), (Ik), (Im), (In), (Io), (Ip), (Iq), (Ir), (Is), (It), (Iu), (Iv), (Iw), (Ix), (Iy), (Iz), (Iad), (Iae), (Iaf), (Iag), (Iah), (Iai), (Iaj), (Iak) (Iam), (Ian), (Iao), (Iap), (Iaq), (Iar), (Ias), (Iat), (Iau), (Iay), (Iaw), (Iax), (Iay), (Iaz), (Iba), (Ibb), (Ibc), (Ibd), (Ibe) or (Ibf) or a cross linked derivative thereof.

In one embodiment there is provided an device containing a polymeric matrix, formed (or obtainable) by exposing a film comprising a compound of the formula (I), (Ia), (Ib), (Ic), (Id), (Ie), (If), (Ig), (Ih), (Ii), (Ij), (Ik), (Im), (In), (Io), (Ip), (Iq), (Ir), (Is), (It), (Iu), (Iv), (Iw), (Ix), (Iy), (Iz), (Iad), (Iae), (Iaf), (Iag), (Iah), (Iai), (Iaj), (Iak) (Iam), (Ian), (Iao), (Iap), (Iaq), (Iar), (Ias), (Iat), (Iau), (Iay), (Iaw), (Iax), (Iay), (Iaz), (Iba), (Ibb), (Ibc), (Ibd), (Ibe) or (Ibf) to radiation, optionally wherein the radiation is ultraviolet light.

In one embodiment there is provided a method for making a device comprising the steps of:
i) dissolving a compound of the formula (I), (Ia), (Ib), (Ic), (Id), (Ie), (If), (Ig), (Ih), (Ii), (Ij), (Ik), (Im), (In), (Io), (Ip), (Iq), (Ir), (Is), (It), (Iu), (Iv), (Iw), (Ix), (Iy), (Iz), (Iad), (Iae), (Iaf), (Iag), (Iah), (Iai), (Iaj), (Iak) (Iam), (Ian), (Iao), (Iap), (Iaq), (Iar), (Ias), (Iat), (Iau), (Iay), (Iaw), (Iax), (Iay), (Iaz), (Iba), (Ibb), (Ibc), (Ibd), (Ibe) or (Ibf) in a suitable organic solvent;
ii) depositing the resultant solution on a substrate;
iii) removing the solvent under evaporation, optionally under reduced pressure to form a film; and
iv) exposing the resultant film to radiation, optionally wherein the radiation is ultraviolet light.

In one embodiment there is provided a method for making a device comprising the steps of:
i) dissolving a compound of the formula (I), (Ia), (Ib), (Ic), (Id), (Ie), (If), (Ig), (Ih), (Ii), (Ij), (Ik), (Im), (In), (Io), (Ip), (Iq), (Ir), (Is), (It), (Iu), (Iv), (Iw), (Ix), (Iy), (Iz), (Iad), (Iae), (Iaf), (Iag), (Iah), (Iai), (Iaj), (Iak) (Iam), (Ian), (Iao), (Iap), (Iaq), (Iar), (Ias), (Iat), (Iau), (Iay), (Iaw), (Iax), (Iay), (Iaz), (Iba), (Ibb), (Ibc), (Ibd), (Ibe) or (Ibf) in a suitable organic solvent;
ii) depositing the resultant solution on a substrate;
iii) removing the solvent under evaporation, optionally under reduced pressure to form a film;
iv) annealing the film by heating at a temperature up to 150° C.,
v) exposing the resultant film to radiation, optionally wherein the radiation is ultraviolet light.

The FIGURE shows current voltage data for a device of the invention in comparison to data for a commercially available polymer.

DETAILED DESCRIPTION OF THE INVENTION

According to one aspect of the invention there is provided a compound of the formula

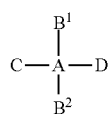

Formula (I)

wherein:
A represents a phenyl group, a naphthyl group, a biphenyl group or two phenyl groups linked by a $C_1$-$C_8$ alkyl chain;
$B^1$ and $B^2$ in each occurrence are independently selected side chains of the structure

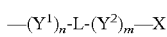
—$(Y^1)_n$-L-$(Y^2)_m$—X wherein:
$Y^1$ and $Y^2$ in each occurrence are independently selected from O, $CO_2$— and $CH_2O$,
m and n in each occurrence are independently selected from 0 or 1;
L in each occurrence is a $C_2$-$C_{14}$ straight chain alkyl group; and X in each occurrence is an independently selected cross linkable group;
C is a side chain of the structure

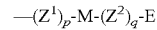
—$(Z^1)_p$-M-$(Z^2)_q$-E wherein:
$Z^1$ and $Z^2$ are independently selected from O, $CO_2$— and $CH_2O$,
p and q in each occurrence are independently selected from 0 or 1;
M is a $C_1$-$C_{14}$ straight chain alkyl group; and
E comprises a charge transport group;
D is a side chain of the structure

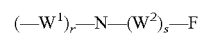
(—$W^1)_r$—N—$(W^2)_s$—F wherein:
$W^1$ and $W^2$ are independently selected from O, $CO_2$— and $CH_2O$,
r and s in each occurrence are independently selected from 0 or 1;
N is a $C_1$-$C_{14}$ straight chain alkyl group; and
F comprises a charge transport group or light emitter group;
and wherein the charge transport group E does not contain a fluorene group other than those that form part of a spirobifluorenearylamine motif.

The compounds of the invention are thus include structures of the following type, wherein the groups $B^1$ and $B^2$ are side chains or arms that terminate in cross linking groups, the groups C is a side chain with charge transport properties and the group D is either a side chain with charge transport properties or a side chain with light emitting properties.

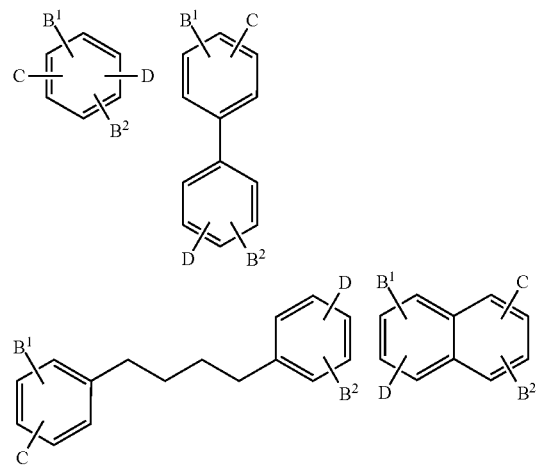

In the instance where the groups C and D are both side chains with charge transport properties they are can be hole transporting groups or electron transporting groups. In some preferred cases the groups C and D are both hole transporting groups, in other preferred cases the groups C and D are both electron transporting groups. In some preferred case the groups C and D are different, in these instances the materials are particular suitable for use as interlayer materials. Interlayer materials have side chains that confer different electronic properties to the group such as the combination of a charge transporting group and an emitter group. These interlayer materials can be chosen to be complementary to adjacent layers thus allowing, for example, devices with reduced switch on voltages compared to the materials known in the art. Reduced switch on voltages can derive from a facilitation of delivery of hole or electrons to the emissive layer of an OLED device. A reduced switch on voltage generally delivers a device with higher efficiency and/or enhanced device lifetime.

One particular advantage of the compounds according to the invention is that they are suitable for solution processing. Compounds according to the invention can thus be dissolved in a suitable organic solvent and deposited onto a substrate to form a film. The relatively high molecular weights of compounds according to the invention provide good film forming properties and this in turn allows films of predictable thickness to be produced. The compounds of the invention are thus well suited to solution processing to deliver devices in a reproducible manner. Furthermore, compounds according to the invention are cross linkable. Thus, once deposited as films on a surface the compounds can be crosslinked, for example by exposing to radiation, such as UV light to form a polymeric matrix that has negligible or at least greatly reduced solubility, this allows excess, none cross-linked material to be washed off the surface. Compounds that can cross link on exposure to radiation, such as UV light, can also be cross linked in a patterned manner by masking parts of the deposited layer from radiation while exposing other parts to the radiation. The compounds of the invention that have cross linking groups that undergo cross linking on exposure to radiation advantageously allow production of devices of highly defined structures in a relatively straightforward manner.

So that the invention may be better understood the nature of the constituent groups and further details of their function is provided herein.

Group A

The group A is an inert central unit upon which side chains or arms that terminate in cross linking groups $B^1$ and $B^2$, and the groups C and D that have other properties (e.g. charge transport properties or light emitting properties) are built. The group A is chosen from phenyl, naphthyl, biphenyl or two phenyl groups linked by a $C_1$-$C_8$ alkyl chain.

In the instances where the group A comprises two phenyl groups linked by a $C_1$-$C_8$ alkyl chain, the $C_1$-$C_8$ alkyl chain can be branched or straight chain and can be chosen from methyl, ethyl, propyl, butyl, pentyl, hexyl, heptyl or octyl, in general straight chain alkyl groups are preferred. It is also preferred that each phenyl group is substituted by two groups selected from C, D, $B^1$ and $B^2$. Furthermore in one preferred instance one phenyl ring is substituted with a cross linkable side chain $B^1$ and a group C whilst the other is substituted with a cross linkable side chain $B^2$ and a group D.

In the instance where the group A is a phenyl group 1,2,4,5-substitution is preferred. Furthermore, in the instance where the group A is a 1,2,4,5-substituted phenyl group it is preferred that the groups C and D are para- to each other.

In the instance where the group A is a naphthyl or biphenyl group it is preferred that each component aromatic ring is substituted by two groups selected from C, D, $B^1$ and $B^2$. In some cases one aromatic ring is substituted with a cross linkable side chain $B^1$ and a group C whilst the other is substituted with a cross linkable side chain $B^2$ and a group D.

Groups $B^1$ and $B^2$ $B^1$ and $B^2$ in each occurrence are independently selected side chains of the structure:

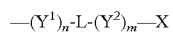

wherein:

$Y^1$ and $Y^2$ in each occurrence are independently selected from O, $CO_2$— and $CH_2O$;

m and n in each occurrence are independently selected from 0 or 1;

L in each occurrence is a $C_2$-$C_{14}$ straight chain alkyl group; and

X in each occurrence is an independently selected cross linkable group.

These groups are side chains of sufficient length to allow the cross linkable groups X located at their termini to cross link with cross linkable groups in adjacent structures on exposure to an initiator, such as radiation, preferably UV light, to form a polymer matrix.

Groups $Y^1$ and $Y^2$ are optional and can be incorporated for synthetic expedience. The groups L are linker groups that are straight chain alkyl groups. In some preferred instances L is a $C_4$-$C_{10}$ straight chain alkyl group. n some preferred instances L is a $C_4$-$C_8$ straight chain alkyl group, for instance butyl, pentyl, hexyl, heptyl or octyl.

Cross Linkable Groups X

The compounds of the invention therefore comprises cross linking group and form, when cross linked, network polymers. This is because preferred cross linking groups react with two other cross linking groups to yield a chain reaction and a polymer matrix.

In a preferred aspect, cross linking groups are selected from the group of ethylenic, diene, thiol and oxetane cross linkable groups. Ethylenic cross linkable groups are cross linkable groups containing a carbon-carbon double bond. In a preferred aspect, all of the cross linking groups independently represent an ethylenic cross linking group. Favoured ethylenic cross linking groups include electron rich and electron poor ethylenic cross linking groups.

In a preferred aspect the cross linkable groups undergo cross linking reaction on exposure to radiation. In a preferred aspect the cross linkable groups undergo cross linking reaction on exposure to ultra-violet (UV) light.

Examples of preferred cross linking groups are straight chain and cyclic α,β-unsaturated esters, α,β-unsaturated amides, vinyl ethers and non-conjugated diene cross linking groups. Favoured cross linking groups therefore include methacrylate, ethacrylate, ethylmaleato, ethylfumarato, N-maleimido, vinyloxy, alkylvinyloxy, vinylmaleato, vinylfumarato, N-(2-vinyloxymaleimido), 1,4-pentadien-3-yl and 1,4-cyclohexadienyl groups.

In a preferred aspect the cross linking groups are electron-rich ethylenic cross linkable groups. Electron rich ethylenic cross linkable groups contain an ethylene group substituted with one or more electron donating groups. The electron donating group can comprise a heteroatom such as O, N or S. In a preferred aspect the electron rich cross linkable group is a vinyloxy group. Other electron donating group substituted crosslinking groups are 1-alkenyl ethers such as propen-1-yloxy groups and buten-1-yloxy groups; cyclic vinyl ethers such as cyclohexen-1-yloxy and cyclopentene-1-yloxy; bicyclic vinyl ethers such as 2-norbornen-2-yloxy groups.

In a preferred aspect the cross linking groups are electron-poor ethylenic cross linkable groups. Electron deficient ethylenic cross linkable groups contain an ethylene group substituted with one or more electron withdrawing groups. The electron withdrawing group may comprise a carbonyl group and may for example be an ester or an amide. In a preferred aspect the electron deficient cross linkable group comprises a monoalkylmaleate group, a monoalkylfumarate group, a monoarylmaleate group, a monoarylfumarate group or a maleimide group. Other examples of electron deficient crosslinking groups are 4,4,4-trifluorocrotonate groups, Z-4,4,4-trifluorobutenoate groups, 3-trifluoromethyl-4,4,4-trifluorocrotonate groups, Z- and E-3-cyanoacrylates, Z- and E-3-cyanomethacrylates, monoalkyl cyclohexene-1,2-dicarboxylates, and monoalkyl cyclopentene-1,2-dicarboxylates.
Group C The compounds of the invention are substituted with a group C that has the structure

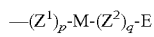

wherein:
$Z^1$ and $Z^2$ are independently selected from O, $CO_2$— and $CH_2O$,
p and q in each occurrence are independently selected from 0 or 1;
M is a $C_1$-$C_{14}$ straight chain alkyl group;
E comprises a charge transport group; and
wherein the charge transport group E does not contain a fluorene group other than those that form part of a spirobifluorenearylamine motif.

In this structure $Z^1$ and $Z^2$ that are independently selected from O, $CO_2$— and $CH_2O$ are groups that may be incorporated for synthetic expedience although they are not always present.

The group M is a linker groups selected from $C_1$-$C_{14}$ straight chain alkyl groups. In some preferred instances M is a $C_4$-$C_{12}$ straight chain alkyl group. In some preferred instances M is a $C_4$-$C_8$ straight chain alkyl group. In some preferred instances M is a $C_4$-$C_8$ straight chain alkyl group, for instance butyl, pentyl, hexyl, heptyl or octyl group. In some instances M is an hexyl group.

The group E is a charge transport group as further described herein.
Charge Transport Groups Charge transport groups according to the invention are groups that confer the ability to transport holes or electrons through an electronic device. These groups are therefore divided into two classes, i) hole transport materials and ii) electron transport materials.
Hole Transport Materials Materials with hole transport properties and the chemical groups that confer hole transport properties are well known in the art. Groups that confer hole transport properties, also referred to herein as hole transport motifs, include triarylamines, e.g. substituted triphenylamines and spirobifluorenearylamines, and carbazoles. Preferred examples of carbazoles are optionally substituted on the central nitrogen and in addition substituted on carbons 3- and 6-, i.e. 3,6-carbazoles, substituted on carbons 2- and 7-, i.e. 2,7-carbazoles, and substituted on carbons 1-, 3-, 6- and 8-, i.e. 1,3,6,8-carbazoles.

Individual hole transport motifs can be joined to additional hole transport motifs to form a chain, either straight or branched, that has enhanced hole transport properties relative to an individual hole transport motif. These chains are also favoured as they increase the overall molecular weight of the structure and this advantageously improves film forming properties. Connection between individual hole transport motifs in the chain is typically by a covalent bond, a phenyl, a fused thiophene or thiophene group. Fused thiophene groups that are suitable for linking individual hole transport motifs include dithieno[3,2-b:2',3'-d] thiophene, benzothiophene and thieno [3,2-b]thiophene. Of these fused thiophene groups thieno[3,2-b]thiophene is preferred. It is also possible to link carbazole units to other hole transport motifs through the nitrogen atom, for example by using a palladium catalysed amination reaction to link to an aromatic halide commonly a bromide, iodide or chloride or an alternative leaving group such as a triflate or mesylate to form a carbon nitrogen bond. These chains of hole transport motifs can be straight or branched and can be constituted from the same type of hole transport motifs, e.g. a chain comprising from two to ten triarylamine motifs, or a combination of two to ten carbazole motifs and triarylamines. The overall chain of hole transport motifs or an individual hole transport motif can optionally be linked to the other components of the C or D chains via an aromatic group, for example via a phenyl, a benzyl, a biphenyl a 2,2'-bithiophene, a thiophene or a fused thiophene group. Fused thiophene groups that are suitable for linking the hole transport motif, or chain of hole transport motifs, to the other components of C and D include dithieno[3,2-b:2',3'-d] thiophene, benzothiophene and thieno [3,2-b]thiophene. Of these fused thiophene groups thieno[3,2-b]thiophene is preferred.

Although there is no requirement for the nitrogen of any carbazole to be substituted this nitrogen group can be substituted with an alkyl group. Alkyl substitution, e.g. $C_1$ to $C_{10}$ alkyl substitution, on the nitrogen atom of the carbazole can be used to fine tune solubility of the overall cross linkable material and can also be used to further improve film forming properties.

Triarylamine hole transport motifs

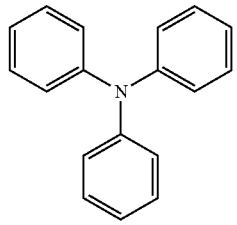

Carbazole hole transport motifs

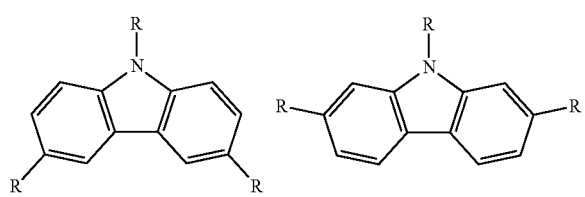

Spirobifluoenearylamine

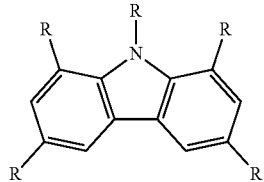

Exemplary structures of hole transporting groups are presented below. The site of attachment to the adjacent component in the C or D side chains is shown as a wavy bond. The groups $R_1$ are individually selected from a hydrogen atom, straight chain or branched achiral $C_1$-$C_{10}$ alkyl or $C_1$-$C_{10}$ haloalkyl, optionally wherein 1, 2, or 3 $CH_2$ groups are replaced an oxygen atom provided no acetal, ketal or peroxide is present in the $R_1$ group. The groups $R_2$ represent a covalent bond, an oxygen

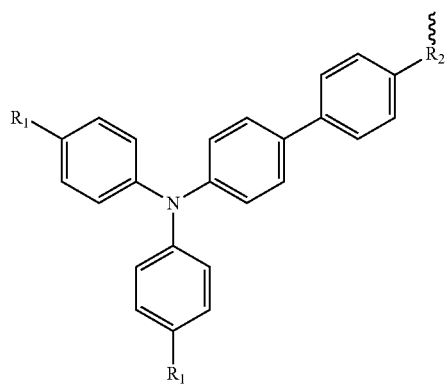

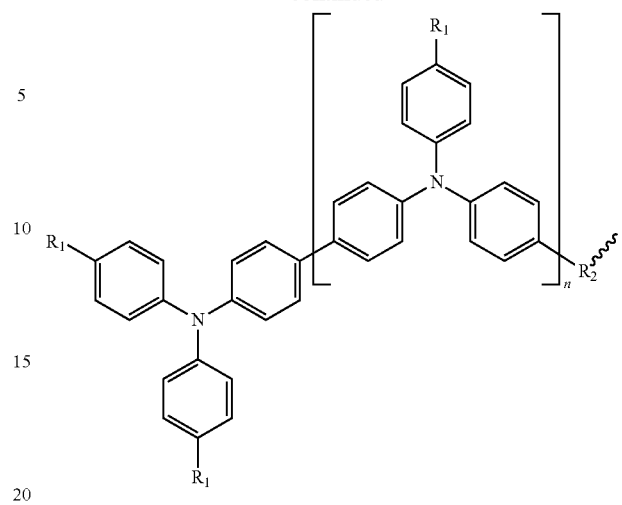
-continued

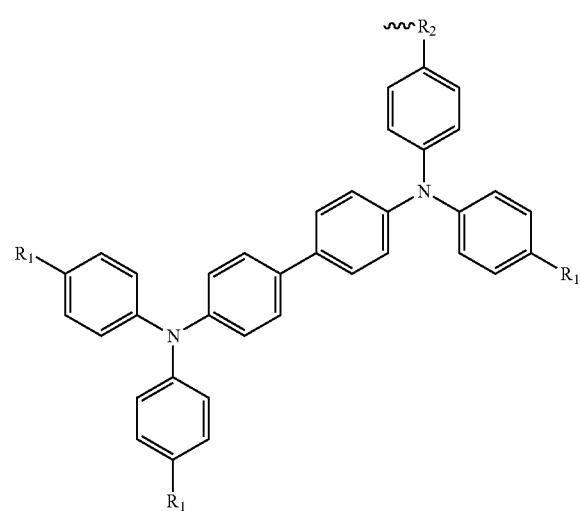

These hole transporting side chains can be prepared by standard methods well known those skilled in the art. Available methods disclosed in the literature (see for example March's Advanced Organic Chemistry: Reactions, Mechanisms, and Structure, Pub Wiley-Blackwell; 7th Edition edition (17 May 2013), ISBN-10: 0470462590) can be readily applied to access the desired structures. Protecting groups, as described in Greene's Protective Groups in Organic Synthesis, Pub Wiley-Blackwell; 5th Edition edition (23 Dec. 2014), ISBN-10: 1118057481, can be used as appropriate. By way of example, palladium catalysed amination reactions can be used for construction of triarylamine hole transport motifs from a diphenylamine precursor as shown below.

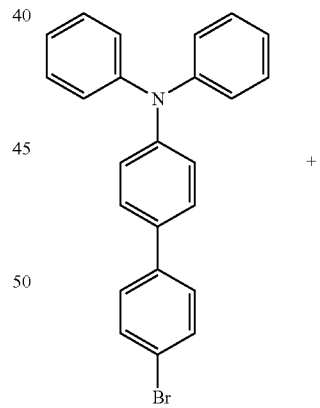

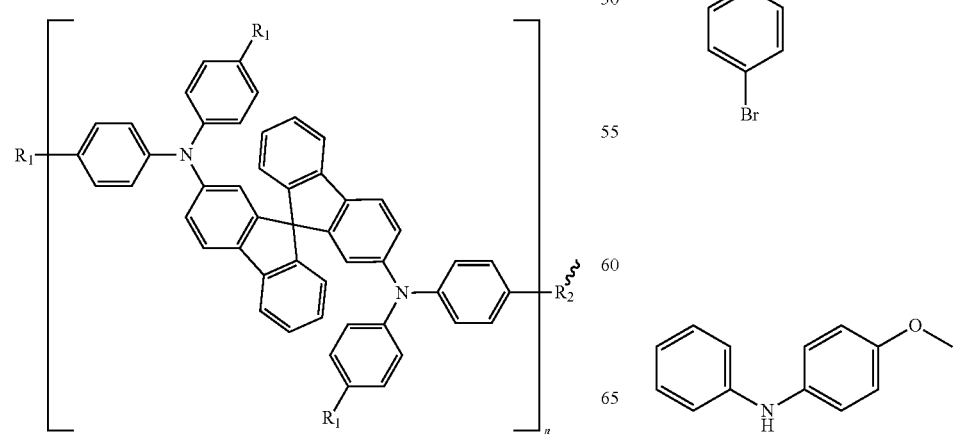

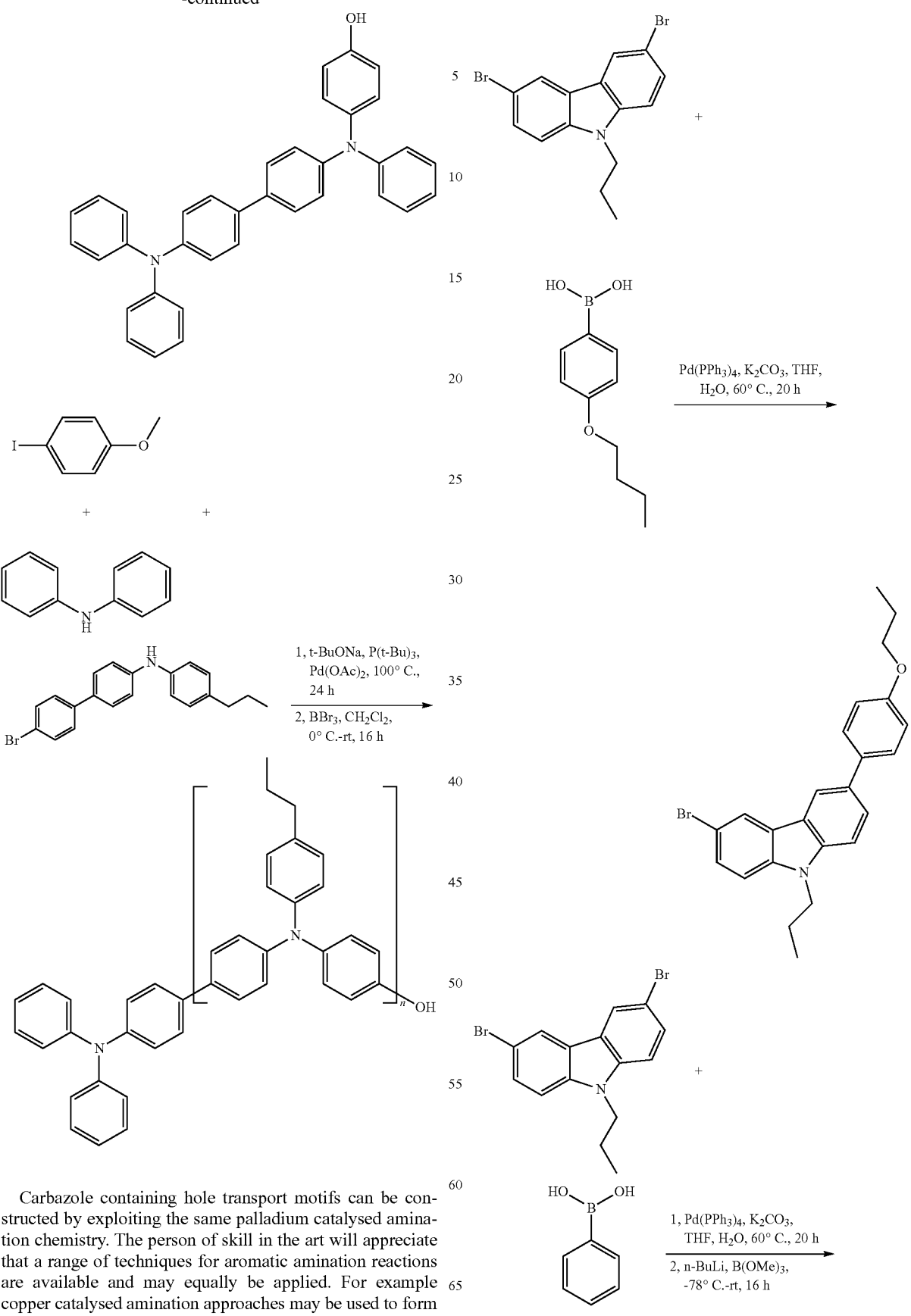

Carbazole containing hole transport motifs can be constructed by exploiting the same palladium catalysed amination chemistry. The person of skill in the art will appreciate that a range of techniques for aromatic amination reactions are available and may equally be applied. For example copper catalysed amination approaches may be used to form triarylamines and substituted carbazoles.

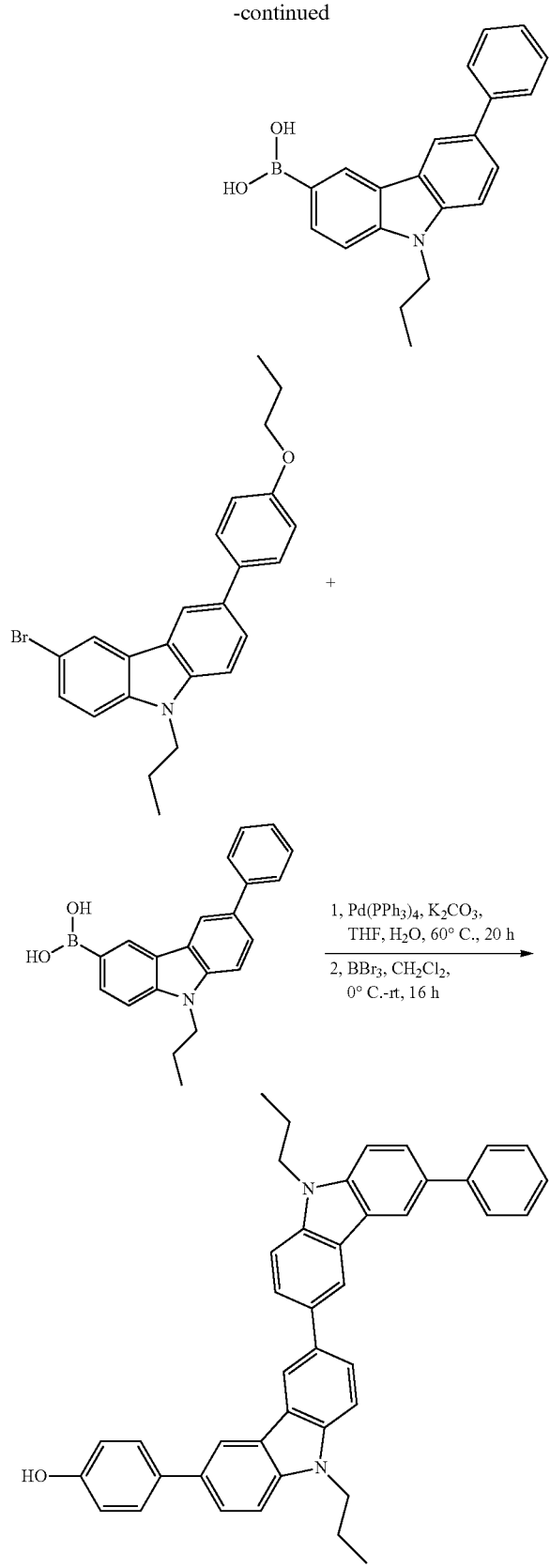

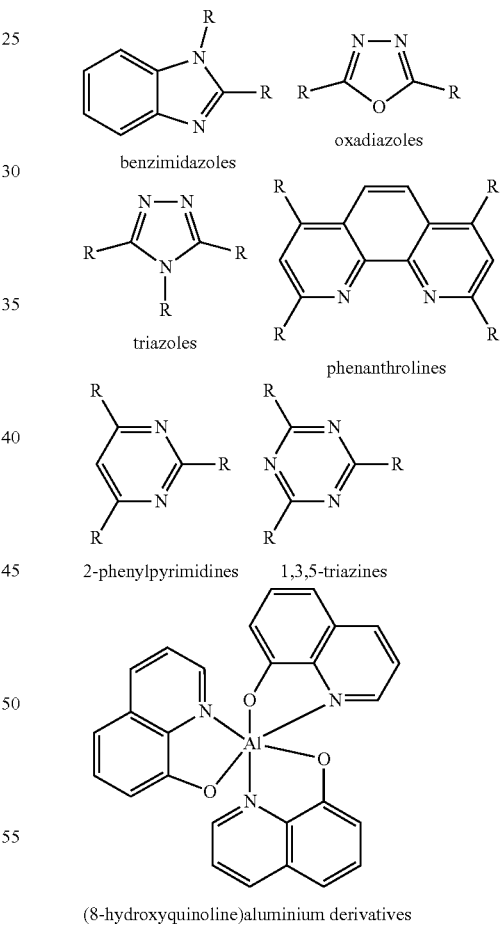

(8-hydroxyquinoline)aluminium derivatives
R denotes typical site of substitution Once these hole transport motifs are elaborated they can be attached to the other components of the C and D chains by standard chemistry such as O-alkylation (e.g. a Williamson ether synthesis), esterification (e.g. under acid catalysis or by using a catalyst such as DCC, EDCI, or from the acid chloride) or by using an alkylation reaction, for example palladium catalysed reaction of an aryl halide or the like with a nucleophile.

Compounds of the invention incorporating hole transport motifs in the groups C and D can be used as hole injection layers as well as hole transport layers.

Electron Transport Materials

Materials with electron transport properties and the chemical groups that confer electron transport properties are well known in the art. Groups that confer electron transport properties, also referred to herein as electron transport motifs, include the group of heterocycles comprising benzimidazoles, oxadiazoles, triazoles, phenanthrolines, 2-phenylpyrimidines, 1,3,5-triazines and thiadiazole and complexes between 8-hydroxyquinolines and aluminium referred to herein as (8-hydroxylquinoline)aluminium groups.

Electron Transport Motifs

In the case of the heterocycle based electron transport motifs, namely those containing at least one benzimidazole, oxadiazole, triazole, phenanthroline, 2-phenylpyrimidine, 1,3,5-triazine and thiadiazole groups or a number of these groups bound together in a chain, these groups are commonly substituted with one or more aryl groups, especially phenyl and biphenyl groups optionally bearing a straight chain or, where possible, a branched chain $C_1$ to $C_5$ alkyl group such as a methyl, ethyl, propyl, butyl, pentyl, hexyl, heptyl or octyl group.

The individual electron transport motifs are either connected directly via a covalent bond or are connected via a phenyl or a $C_1$-$C_5$ heterocyclic group. The term $C_1$-$C_5$ heterocycle and $C_1$-$C_5$ heterocyclic group as used herein and throughout the specification refers to 5- and 6-membered aromatic heterocyclic groups containing at least one carbon atom with the other atoms in the ring being selected from nitrogen, sulphur and oxygen. Examples of 5-membered aromatic $C_1$-$C_5$ heterocycles include tetrazole, triazole, oxadiazole, thiadiazole, imidazole, oxazole, thiazole, pyrrole, furan and thiophene. Examples of 6-membered aromatic $C_1$-$C_5$ heterocycles include pyridine, pyrimidine and triazine. Preferred aromatic $C_1$-$C_5$ heterocycles contain between one and three heteroatoms selected from nitrogen, oxygen and sulphur.

The overall chain of electron transport motifs or an individual electron transport motif can be linked to the other components of the C or D chains via a covalent bond, phenyl group or a biphenyl group.

The overall chain of electron transport motifs or an individual electron transport motif can terminate in a $C_1$-$C_8$ alkyl group, a phenyl group optionally substituted with a $C_1$-$C_8$ alkyl group or biphenyl group optionally substituted with a $C_1$-$C_8$ alkyl group Accordingly the compounds of the invention include examples wherein the electron transport motif is of the general formula:

—$(Ar^1)_m$-$(Het$-$Ar^2)_n$—$(Ar^3)_q$ wherein $Ar^1$ is an independently selected phenyl or biphenyl group;

m=0 or 1;

Het in each occurrence denotes a covalent bond or a heterocycle selected from benzimidazole, oxadiazole, triazole, phenanthroline, 2-phenylpyrimidine, 1,3,5-triazine and thiadiazole provided that at least one heterocycle selected from benzimidazole, oxadiazole, triazole, phenanthroline, 2-phenylpyrimidine, 1,3,5-triazine and thiadiazole is present;

$Ar^2$ is in each occurrence selected from a covalent bond, a phenyl group, a $C_1$-$C_5$ heterocycle;

n is an integer from 1 to 10;

$Ar^3$ is i) H or a $C_1$-$C_8$ alkyl group, ii) an optionally substituted phenyl group or iii) an optionally substituted biphenyl group, wherein the optional substituent in cases ii) and iii) is a $C_1$-$C_8$ alkyl group;

provided that no more than ten benzimidazole, oxadiazole, triazole, phenanthroline, 2-phenylpyrimidine, 1,3,5-triazine and thiadiazole groups are present in each of the groups E and F.

q in the definition of $Ar^3$ is preferably 1.

The invention equally encompasses examples where the chain is branched, for example where

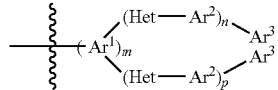

wherein $Ar^1$ is an independently selected phenyl or biphenyl group;

m=1;

Het in each occurrence denotes a covalent bond or a heterocycle selected from benzimidazole, oxadiazole, triazole, phenanthroline, 2-phenylpyrimidine, 1,3,5-triazine and thiadiazole provided that at least one heterocycle selected from benzimidazole, oxadiazole, triazole, phenanthroline, 2-phenylpyrimidine, 1,3,5-triazine and thiadiazole is present;

$Ar^2$ is in each occurrence selected from a covalent bond, a phenyl group, a $C_1$-$C_5$ heterocycle;

n and p are an integer from 1 to 9, wherein n+p is from 2 to 10;

$Ar^3$ is in each case i) H or a $C_1$-$C_8$ alkyl group, ii) an optionally substituted phenyl group or iii) an optionally substituted biphenyl group, wherein the optional substituent in cases ii) and iii) is a $C_1$-$C_8$ alkyl group;

provided that no more than ten benzimidazole, oxadiazole, triazole, phenanthroline, 2-phenylpyrimidine, 1,3,5-triazine and thiadiazole groups are present in each of the groups E and F.

The invention equally includes compounds with electron transport motifs of the general structure

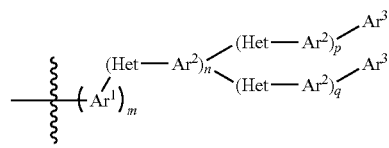

wherein $Ar^1$ is an independently selected phenyl or biphenyl group;

m=0 or 1;

Het in each occurrence denotes a covalent bond or a heterocycle selected from benzimidazole, oxadiazole, triazole, phenanthroline, 2-phenylpyrimidine, 1,3,5-triazine and thiadiazole provided that at least one heterocycle selected from benzimidazole, oxadiazole, triazole, phenanthroline, 2-phenylpyrimidine, 1,3,5-triazine and thiadiazole is present;

$Ar^2$ is in each occurrence is selected from a covalent bond, a phenyl group, a $C_1$-$C_5$ heterocycle;

n and p are integers from 1 to 8, wherein n+p+q is from 3 to 10, and wherein n is greater than or equal to 1;

$Ar^3$ is in each case i) H or a $C_1$-$C_8$ alkyl group, ii) an optionally substituted phenyl group or iii) an optionally substituted biphenyl group, wherein the optional substituent in cases ii) and iii) is a $C_1$-$C_8$ alkyl group;

provided that no more than ten benzimidazole, oxadiazole, triazole, phenanthroline, 2-phenylpyrimidine, 1,3,5-triazine and thiadiazole groups are present in each of the groups E and F.

As will be appreciated by those skilled in the art, the provision of electron transport properties is conferred by the presence of a number of electron transfer motifs rather than the precise geometrical arrangement of these motifs in the structure. It is preferred that groups are nonetheless highly conjugated, preferably fully conjugated, to allow extensive charge delocalisation in the electron transport motif. Thus the preferred heterocycles are to be linked preferably by covalent bonds, by phenyl groups or by $C_1$-$C_5$ heterocycle groups.

Individual electron transport motifs can be joined to additional electron transport motifs to form a chain that has enhanced electron transport properties relative to an individual electron transport motif. In such chains the heterocyclic groups, i.e. the benzimidazole, oxadiazole, triazole, phenanthroline, 2-phenylpyrimidine, 1,3,5-triazine and thiadiazole groups can be directly linked, i.e. by a covalent bond, or they can be connected by a phenyl group or $C_1$-$C_5$ heterocycle linkages. Such chains of electron transport motifs are generally favoured as they increase the overall molecular weight of the structure and this advantageously improves their film forming properties.

In some preferred instances individual electron transport motifs in the chain are connected by covalent bonds or phenyl linkages. In some preferred instances individual electron transport motifs in the chain are connected by covalent bonds, phenyl, or $C_1$-$C_5$ heterocycle linkages. These chains of electron transport motifs can be straight or branched and can be constituted from the same type of electron transport motifs, e.g. a chain comprising from two to ten heterocycle units selected from benzimidazole, oxadiazole, triazole, phenanthroline, 2-phenylpyrimidine, 1,3,5-triazine and thiadiazole motifs, or a combination of two to ten heterocycle units selected from benzimidazole, oxadiazole, triazole, phenanthroline, 2-phenylpyrimidine, 1,3,5-triazine and thiadiazole motifs. The overall chain or individual motif can optionally be linked to the other components of the C or D chains via an aromatic group, for example via a phenyl, a biphenyl or a naphthyl. Although there is no requirement for the nitrogen at N-1 of any benzimidazole to be substituted this nitrogen group can be substituted with an alkyl group. Alkyl substitution on the nitrogen atom of the benzimidazole can be used to fine tune solubility of the overall cross linkable material and can also be used to further improve film forming properties. Alternatively the benzimidazole can be conveniently us as a site for branching with further substituents being attached, for example, at N-1 and C-2.

Some exemplary compounds according to the invention are provided below. As an example, compounds of the invention with electron transporting properties features oxadiazole, oxadiazole, benzimidazole and (8-hydroxylquinoline) aluminium motifs in the side chains C and D.

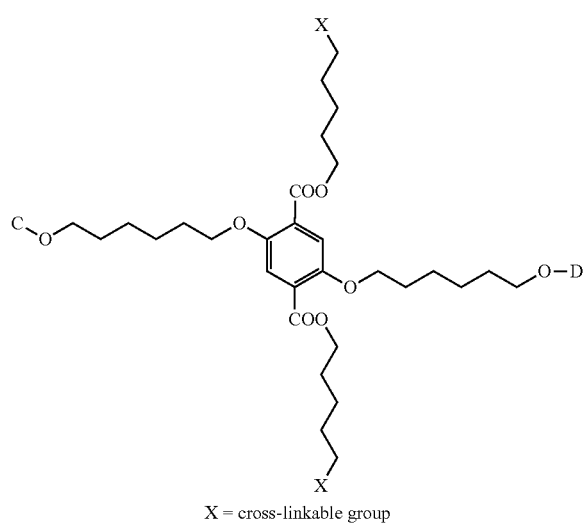

X = cross-linkable group

Electron transporting groups according to the invention can be made by conventional synthetic techniques well known to those skilled in the art. In a simple example the groups E and F can be attached to cores bearing the other components of the C and D chains via a Williamson ether synthesis as shown in the scheme below.

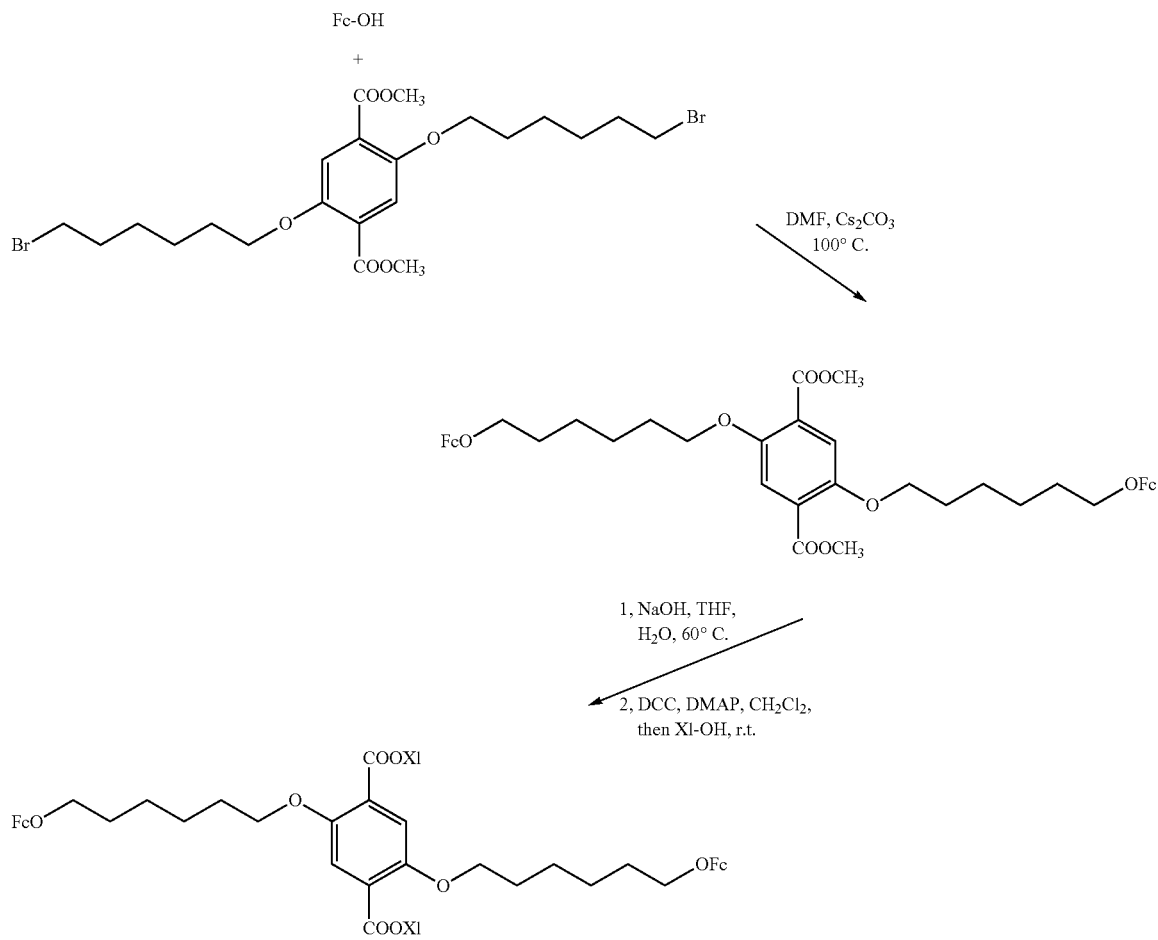
An exemplary functional unit (an electron transporter), 3,5-bis(1-methyl-1H-benzo[d]imidazol-2-yl)phenol for incorporation into the C and/or D group can be prepared as shown in the scheme below.
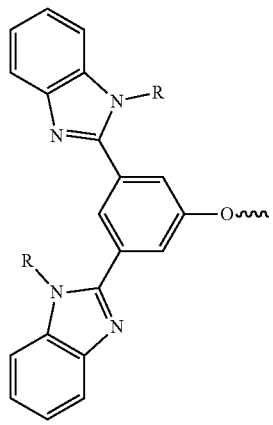
FUNCTIONAL UNIT
R = C1 (CH$_3$) to C10 (C$_{10}$H$_{21}$)
R = phenyl, biphenyl, naphthyl

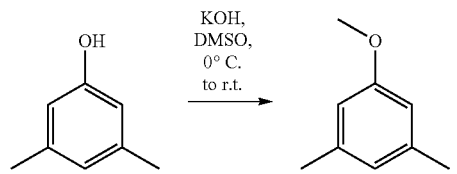
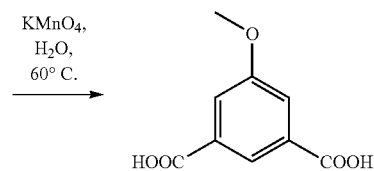
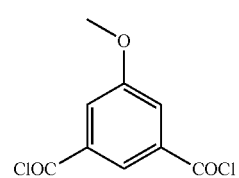
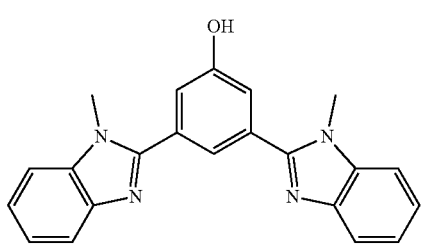
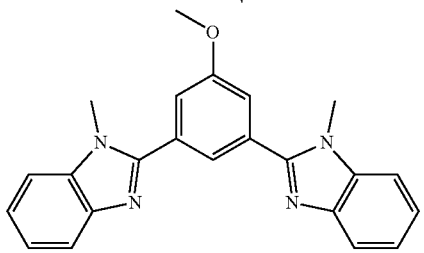
A further exemplary functional unit (an electron transporter), 4'45-(4-(tert-butyl)phenyl)-1,3,4-oxadiazol-2-yl)-[1,1'-biphenyl]-4-ol for incorporation into the C and/or D group can be prepared as shown in the scheme below.
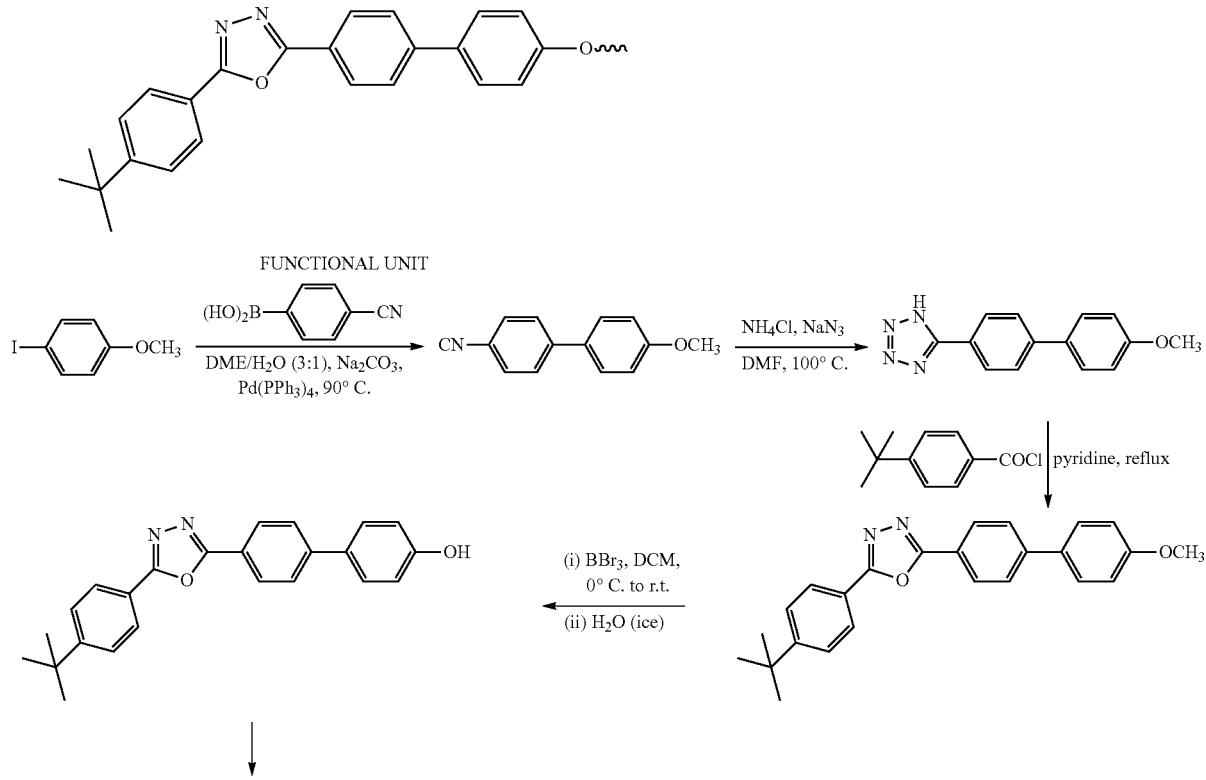

A further exemplary functional unit (an electron transporter), 4'-(5-(4-(tert-butyl)phenyl)-4-phenyl-4H-1,2,4-triazol-3-yl)-[1,1'-biphenyl]-4-ol for incorporation into the C and/or D group can be prepared as shown in the scheme below.

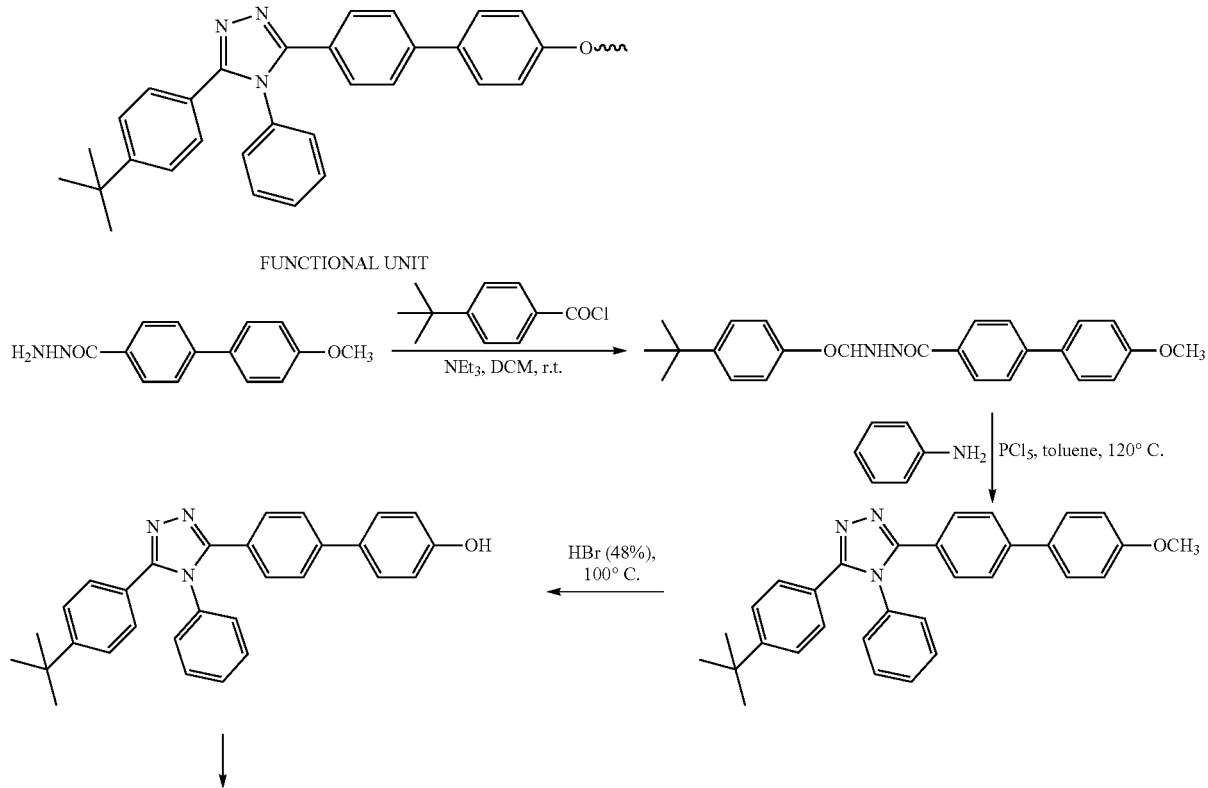

FUNCTIONAL UNIT

Further examples of electron transporting motifs with groups E and F are shown below.

Benzimidazoles

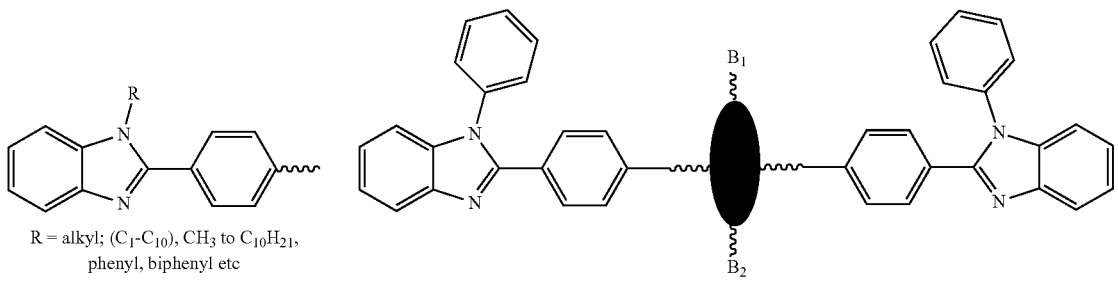

R = alkyl; (C$_1$-C$_{10}$), CH$_3$ to C$_{10}$H$_{21}$, phenyl, biphenyl etc

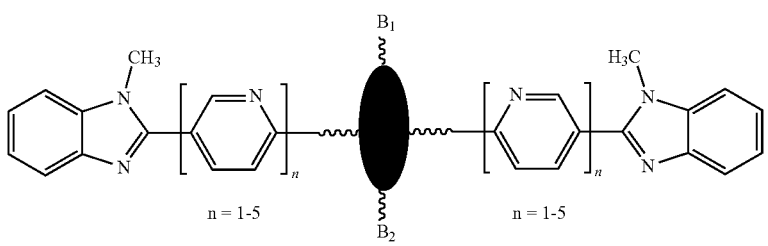

n = 1-5         n = 1-5

-continued
Oxadiazoles
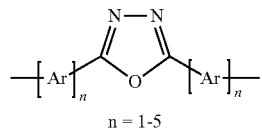
n = 1-5
Ar = phenyl, pyridine,
pyrimidine,
fluorene, carbazole
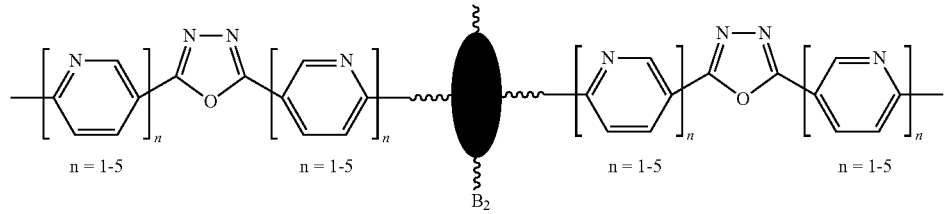
n = 1-5    n = 1-5    n = 1-5    n = 1-5
Triazoles
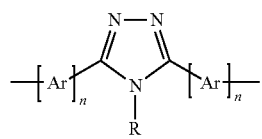
n = 1-5
Ar = phenyl, pyridine etc
R = alkyl ($C_1$-$C_8$),
phenyl, biphenyl etc
Phenanthrolines
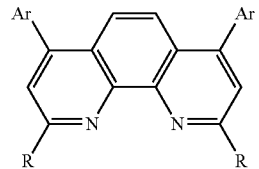
Ar = phenyl, pyridine,
pyrimidine,
fluorene, carbazole
R = $C_1$-$C_{10}$ ($CH_3$—$C_{10}H_{21}$)
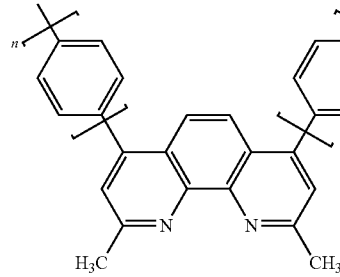
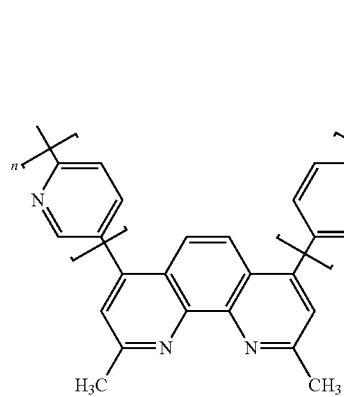
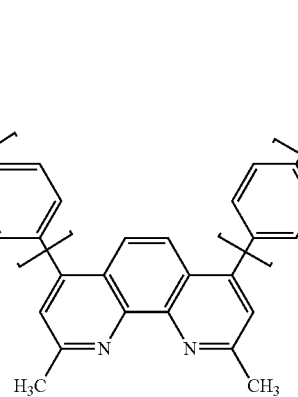

Group D

D is a side chain of the structure

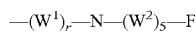

—(W$^1$)$_r$—N—(W$^2$)$_s$—F wherein:

W$^1$ and W$^2$ are independently selected from O, CO$_2$— and CH$_2$O, r and s in each occurrence are independently selected from 0 or 1;

N is a C$_1$-C$_{14}$ straight chain alkyl group; and

F comprises a charge transport group or light emitter group;

In the instance where F comprises a charge transporting group, the group D and its constituents corresponds to the group C and its constituents as described above.

Compounds with a group D that comprises a light emitting group are particularly advantageous for use as an interface layer between the emitting layer of an OLED and the adjacent charge transport layer(s). This is because the blend of charge transport and light emitting properties allows efficient transport of electrons and holes into the emitting layer and this, advantageously, can reduce the voltage that is required to trigger emission. As a result of this property, that is believed from the favoured mixing of the D group of materials of the present invention with complementary light emitter materials, the materials of the invention can be used to deliver devices with reduced "turn-on" voltages. As reducing the voltage required to turn on the device and maintain light emission is an important determinant of OLED device lifetime, enhanced OLED device lifetimes can be obtained by use of the materials of the invention.

The advantages of these hybrid materials where C is a charge transporting and D is light-emitting include the following: i) these materials provide the ability to control/tune the charge injection/transporting properties of a fluorophore that might have poor charge transporting properties alone but can be improved within this hybrid structural architecture; ii) a fluorophore with good hole-injection/transporting properties but poor electron injection/transporting can be improved by incorporating an efficient electron-accepting/transporting moiety into the structure; iii) a fluorophore with good electron-injection/transporting properties but poor hole-injection/transporting can be improved by incorporating an efficient hole-accepting/transporting moiety into the structure; and iv) the potential to combine charge transport properties and light emitting properties in a single molecule wherein the groups that confer each property are electronically isolated from each other (i.e., electronically isolating (non-conjugated) a fluorophore moiety and charge transporting moiety in a single molecule, can be advantageous over a two-component system (one charge transporting material added to a light-emitting material) that can be prone to phase segregation. Phase segmentation can be detrimental to OLED device perform, for example these can lead to the need to use increased turn on voltages and this, correspondingly, can compromise device lifetime. In addition, all the previously noted advantages regarding device fabrication are still applicable. Solution phase processing is thus possible with these hybrid materials and the materials have good film forming properties as a result of their combination of reasonably high molecule weight and solubility. Patterned structures can be formed via triggering cross linking via radiation, such as UV light, in combination with masking techniques.

Light Emitting Motifs

In the instance wherein the group D is a light emitting group then any suitable motif known in the art may be selected. One particularly preferred type of light emitting motif are those described PCT/GB2015/051164. Details of how such motifs can be synthesised are provided therein.

For example light emitting group F can be a light emitting group comprising a group FL of the structure

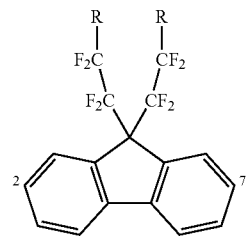

wherein the R groups of each FL moiety are identical and are selected from the group consisting of straight chain or branched achiral C$_1$-C$_{14}$ alkyl, C$_1$-C$_{14}$ haloalkyl, C$_1$-C$_{14}$ fluoroalkyl, C$_2$-C$_{14}$ alkenyl group, optionally wherein 1, 2, 3, 4 or 5 CH$_2$ groups are replaced by an oxygen provided that no acetal, ketal, peroxide or vinyl ether is present in the R group.

In a related example the group F can be a light emitting group of the structure

—Ar$^1$-(FL-Ar$^2$)$_n$-Q that comprises from 1 to 8 FL groups and wherein the dash at the left hand side indicates the site of connection to the other components of the group F;

wherein Ar$^1$ and Ar$^2$ in each occurrence are independently selected from the group comprising Ar$^a$ and a bond;

Ar$^a$ represents a diradical comprising 1 aromatic, heteroaromatic or FL moiety, or 2, 3, 4 or 5 aromatic, heteroaromatic and/or FL moieties mutually connected by a single bond;

n is an integer from 1 to 8;

Q is a hydrogen, C$_1$-C$_{14}$ alkyl, C$_1$-C$_{14}$ haloalkyl or C$_1$-C$_{14}$ fluoroalkyl group;

FL is a fluorene moiety of the structure

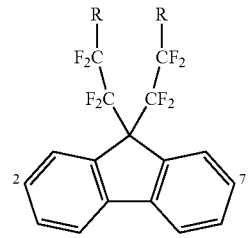

incorporated into the chain through covalent bonds at C-2 and C-7, the R groups of each FL moiety are identical and are selected from the group consisting of straight chain or branched achiral C$_1$-C$_{14}$ alkyl, C$_1$-C$_{14}$ haloalkyl, C$_1$-C$_{14}$ fluoroalkyl, C$_2$-C$_{14}$ alkenyl group, optionally wherein 1, 2, 3, 4 or 5 CH$_2$ groups are replaced by an oxygen provided that no acetal, ketal, peroxide or vinyl ether is present in the R group.

Material Properties

The materials of the present invention are particularly useful for their charge transport. As such the materials described herein are useful in the fabrication of electronic devices, for example organic light emitting diodes, organic field effect transistors and photovoltaic devices.

One advantageous property of the oligomeric materials of the present invention is that they are soluble in common organic solvents. Typical hydrocarbon solvents in which the compounds of the invention dissolve include benzene, toluene or xylene or halogenated derivatives thereof such as chlorobenzene. This solubility is significant as the solubility properties of the oligomers provides a distinct advantage in terms of device fabrication relative to e.g. polymeric materials that are relatively insoluble or not soluble at all. In more detail, these oligomeric material may be used to fabricate devices via a solution processing approach. In outline, this involves first dissolving the material, applying this solution to a substrate and then evaporating to generate a film coating on the substrate. Once the material is deposited as a film the material can be polymerised in situ. This polymerisation may be initiated by exposure to radiation, for instance ultraviolet light, which causes the cross linkable groups of one molecule to cross link with those in an adjacent molecule to form a network polymer. Regions of the deposited film can be masked from the initiating radiation to give zones of non cross-linked material while zones exposed to radiation undergo polymerisation. If desired the unexposed, non-cross linked material can be washed off to leave behind a patterned structure of cross linked material due to the cross linked material having negligible or reduced solubility relative to that of the monomer. Iterative cycles of solution deposition and polymerisation and, if required, washing can be used to generate structures with complex architectures.

Sequentially deposited polymerised structures can be assembled in a side by side or stacked/layered manner. In one example, sequential deposition and polymerisation of red, green and blue emitting material in a side by side manner can be used to generate pixels for colour displays. In another example, a stack of red, green and blue emitter materials can be used to give a white light source. In another example, two or more emitter structures can be arranged in a stack to give a coloured light source.

The ability to cheaply and economically produce multi-layer devices in which adjoining layers have different highest occupied or lowest unoccupied molecular orbital (HOMO and LUMO) energy levels as well as different charge carrier mobilities is of general utility in plastic electronics. For instance, the equivalent of p-n junctions may be formed using the materials and processes of this invention and these may find utility in diodes, transistors, and photovoltaic devices. The propensity of the materials of the invention to be photo lithographically patterned allows large arrays of plastic electronic devices of virtually any size and description to be fabricated.

Yet another advantage of using mixtures of the materials of the invention is that it allows the use of mixtures of materials in which photoinitiated electron donor/acceptor interactions as opposed to ionic or free radical initiation are used to initiate polymerization. This may result in much more stable (in terms of shelf-life) materials than in methacrylate-based systems, while at the same time maintaining low UV crosslinking fluences. In these mixtures at least one of the materials is substituted with electron-rich crosslinking groups while at least one other component material is substituted with electron-deficient crosslinking groups. Ultraviolet radiation incident on the material promotes the electron deficient crosslinking groups on some molecules into electronically excited states. The excited state, electron-deficient crosslinking groups then abstract electrons from the electron-rich (electron donor) crosslinking groups on other molecules initiating the copolymerization crosslinking reaction. Descriptions of this mode of photopolymerization may be found in, for example, "Photoinitiated radical polymerization of vinyl ether-maleate systems", Polymer 38, (9) pp. 2229-37 (1997); and "Co-Polymerization of Maleimides and Vinyl Ethers: A Structural Study", Macromolecules 1998, (31) pp. 5681-89.

Electron-deficient crosslinking groups include maleimides, maleates, fumarates, and other unsaturated esters. Electron donor groups include vinyl ethers, propenyl ethers and other similar alkenyl ethers. Mixtures like these are advantageous in that the individual components are thermally and photochemically stable with excellent shelf lives. However, when the materials are combined, the mixture has high photochemical sensitivity and requires only a relatively small UV dose for crosslinking.

An exemplary process for making a device from the materials of the invention would typically comprise the steps of: i) dissolving a the compound of the invention in a suitable organic solvent; ii) depositing the resultant solution on a substrate; iii) removing the solvent under evaporation, optionally under reduced pressure to form a film; and iv) exposing the resultant film to radiation, optionally wherein the radiation is ultraviolet light. Optionally the process can involve the step of annealing the film by heating at a temperature from 40° C. to 150° C. Optionally the process can involve partially masking the film prior to exposure radiation thereby allowing a patterned cross linking of only portions of the film exposed to the radiation.

SYNTHETIC EXAMPLES

The compounds of the present invention may be synthesised by common techniques in organic synthesis well known to those of ordinary skill in the art. Illustrative examples of how these compounds can be synthesised are presented below. As can be appreciated, the nature of these materials allows a modular approach to synthesis to be adopted. Each component A, B, C and D can be adjusted to fine tune the electronic, film forming and solubility properties of the material. The examples provided below are by way of example only and in no way limit the scope of the invention.

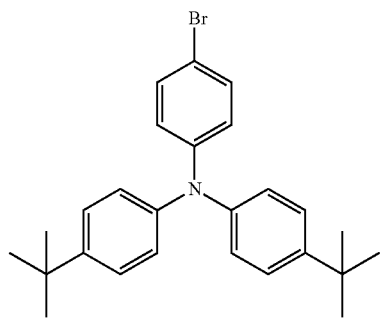 [SMILES: CC(C)(C)c1ccc(N(c2ccc(Br)cc2)c2ccc(C(C)(C)C)cc2)cc1]

Synthesis of Compound 1

Pd$_2$(dba)$_3$ (0.16 g, 0.18 mmol) and BINAP (0.33 g, 0.53 mmol) were mixed in 5 mL of dry toluene and stirred under argon for 20 min. After which 1,4-dibromobenzene (1.7 g, 7.1 mmol), bis(4-t-butylphenyl)amine (2.0 g, 7.1 mmol), sodium t-butoxide (0.96 g, 10 mmol) and dry toluene (25 mL) were added and the mixture was stirred at 90° C. for 18 h. After the mixture was allowed to cool to room temperature it was diluted with water (100 mL) and the layers were separated. The aqueous layer was then extracted with diethyl ether (3×50 mL) and the combined organics were dried (MgSO$_4$), filtered and evaporated to dryness under reduced pressure. The crude product was purified by flash chromatography (5%-7.5% dichloromethane in hexane) which yielded the product as a white solid (1.8 g, 4.1 mmol, 58%). $^1$H NMR (400 MHz, CDCl$_3$), δ=1.31 (18H, s, CH$_3$), 6.91-6.93 (2H, m, Ar—H), 6.98-7.01 (4H, m, Ar—H), 7.24-7.27 (4H, m, Ar—H), 7.28-7.30 (2H, m, Ar—H).

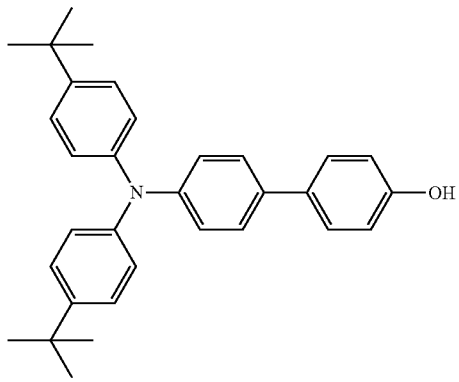 [SMILES: CC(C)(C)c1ccc(N(c2ccc(-c3ccc(O)cc3)cc2)c2ccc(C(C)(C)C)cc2)cc1]

Synthesis of Compound 2

Pd(PPh$_3$)$_4$ (0.47 g, 0.40 mmol) was added to a stirred solution of compound 1 (1.8 g, 4.0 mmol) and 4-hydroxyphenyl boronic acid (0.83 g, 6.1 mmol) in degassed dioxane (20 mL) and Na$_2$CO$_3$ (2.1 g, 20 mmol) in degassed water (5 mL). The reaction mixture was stirred at reflux for 16 h. After which the mixture was allowed to cool to room temperature and the solvent was then removed under reduced pressure. The residue was redissolved in dichloromethane (50 mL) and washed with 1 M NaOH solution in water (3×50 mL), followed by washing with 1 M HCl (2×50 mL). The organic layer was then dried (MgSO$_4$), filtered and evaporated to dryness under reduced pressure. The crude product was purified by flash chromatography (10% ethyl acetate in hexane), which yielded the product as a red/brown solid (0.75 g, 1.7 mmol, 41%). $^1$H NMR (400 MHz, CDCl$_3$), δ=1.32 (18H, s, CH$_3$), 6.87-6.89 (2H, br d, J=8.5 Hz, Ar—H), 7.04-7.06 (4H, br d, J=8.7 Hz, Ar—H), 7.09-7.11 (2H, br d, J=8.5 Hz, Ar—H), 7.25-7.27 (4H, br d, J=8.5 Hz, Ar—H), 7.38-7.40 (2H, br d, J=8.7 Hz, Ar—H), 7.43-7.45 (2H, br d, J=8.5 Hz, Ar—H).

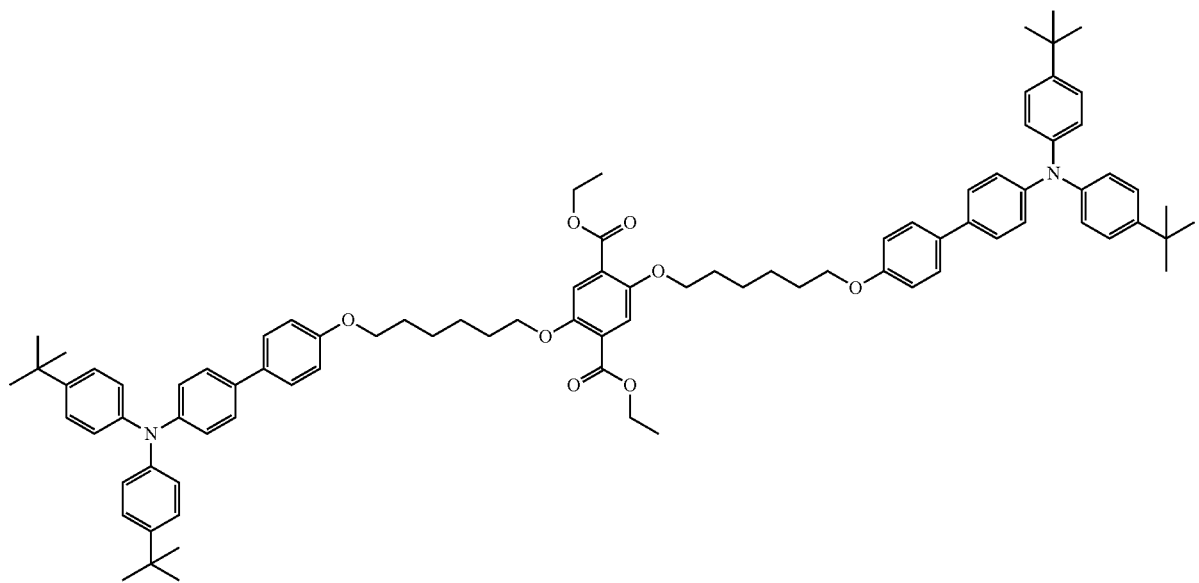 [SMILES: CCOC(=O)c1cc(OCCCCCCOc2ccc(-c3ccc(N(c4ccc(C(C)(C)C)cc4)c4ccc(C(C)(C)C)cc4)cc3)cc2)c(C(=O)OCC)cc1OCCCCCCOc1ccc(-c2ccc(N(c3ccc(C(C)(C)C)cc3)c3ccc(C(C)(C)C)cc3)cc2)cc1]

Synthesis of Compound 3

A mixture of diethyl-2,5-di(bromohexyl)oxyterephthalate (0.45 g, 0.78 mmol), compound 2 (0.74 g, 1.7 mmol) and $Cs_2CO_3$ (1.5 g, 4.7 mmol) in dry DMF (25 mL) was heated to 90° C. under argon and stirred for 16 h. After which the solvent was removed under reduced pressure and the residue was dissolved in dichloromethane (50 mL). The suspension was then filtered and the filtrate was evaporated to dryness under reduced pressure. The crude product was purified by flash chromatography (40% hexane in dichloromethane), which yielded the product as a white solid (0.83 g, 0.63 mmol, 80%). $^1$H NMR (400 MHz, $CDCl_3$), δ=1.32 (36H, s, $CH_3$), 1.38 (6H, t, J=7.1 Hz, $CH_3$), 1.56-1.57 (8H, m, $CH_2$), 1.80-1.88 (8H, m, $CH_2$), 3.98-4.04 (8H, m, $CH_2$), 4.37 (4H, q, J=7.1 Hz, $CH_2$), 6.94 (4H, br d, J=8.8 Hz, Ar—H), 7.05 (8H, br d, J=8.7 Hz, Ar—H), 7.10 (4H, br d, J=8.7 Hz, Ar—H), 7.26 (8H, br d, J=8.7 Hz, Ar—H), 7.35 (2H, s, Ar—H), 7.40 (4H, br d, J=8.7 Hz, Ar—H), 7.47 (4H, br d, J=8.8 Hz, Ar—H).

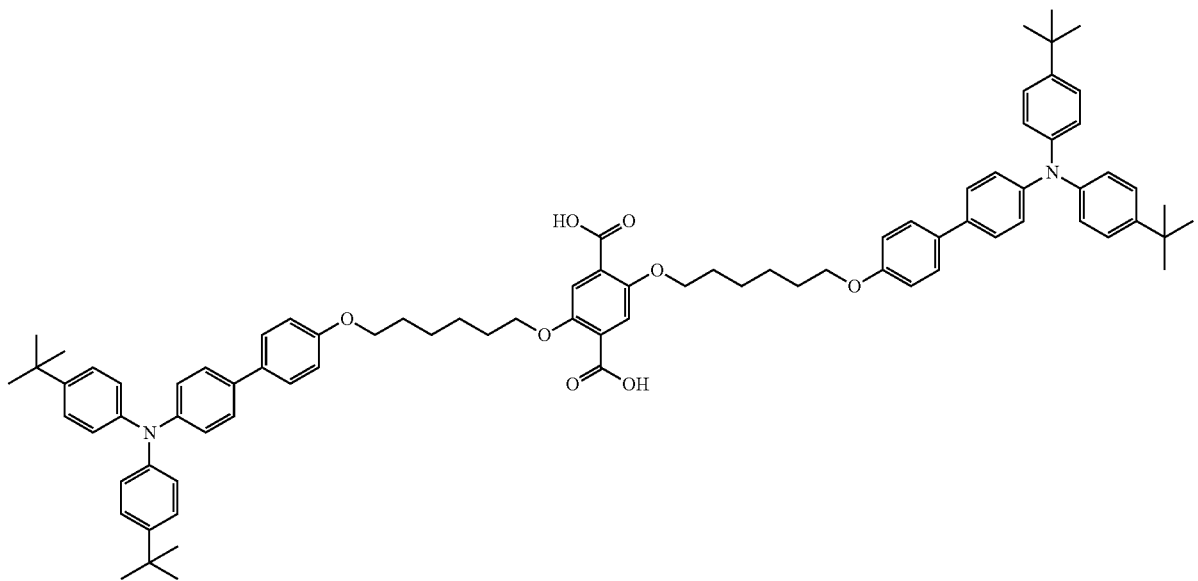 [SMILES: CC(C)(C)c1ccc(N(c2ccc(-c3ccc(OCCCCCCOc4cc(C(=O)O)c(OCCCCCCOc5ccc(-c6ccc(N(c7ccc(C(C)(C)C)cc7)c7ccc(C(C)(C)C)cc7)cc6)cc5)cc4C(=O)O)cc3)cc2)c2ccc(C(C)(C)C)cc2)cc1]

Synthesis of Compound 4

An aqueous solution of NaOH (1 M, 10 mL) was added to a stirred solution of compound 3 (0.83 g, 0.63 mmol) in tetrahydrofuran (20 mL) was stirred at 60° C. for 2 days. On completion the solution was acidified with 2 M HCl and then the product was extracted with dichloromethane (3×50 mL). The combined organics were dried (MgSO4), filtered and the solvent was removed under reduced pressure. This yielded the product as an off white solid (0.77 g, 0.61 mmol, 97%). $^1$H NMR (400 MHz, CDCl$_3$), δ=1.32 (36H, s, CH$_3$), 1.58-1.60 (8H, m, CH$_2$), 1.82-1.86 (4H, m, CH$_2$), 1.94-2.01 (4H, m, CH$_2$), 4.01 (4H, t, J=6.2 Hz, CH$_2$), 4.32 (4H, t, J=6.5 Hz, CH$_2$), 6.93 (4H, br d, J=8.7 Hz, Ar—H), 7.05 (8H, br d, J=8.5 Hz, Ar—H), 7.10 (4H, br d, J=8.5 Hz, Ar—H), 7.26 (8H, br d, J=8.5 Hz, Ar—H), 7.40 (4H, br d, J=8.5 Hz, Ar—H), 7.47 (4H, br d, J=8.7 Hz, Ar—H), 7.9 (2H, s, Ar—H); MS (MALDI+): m/z calculated for [M]$^+$=1260.7, found 1260.5.

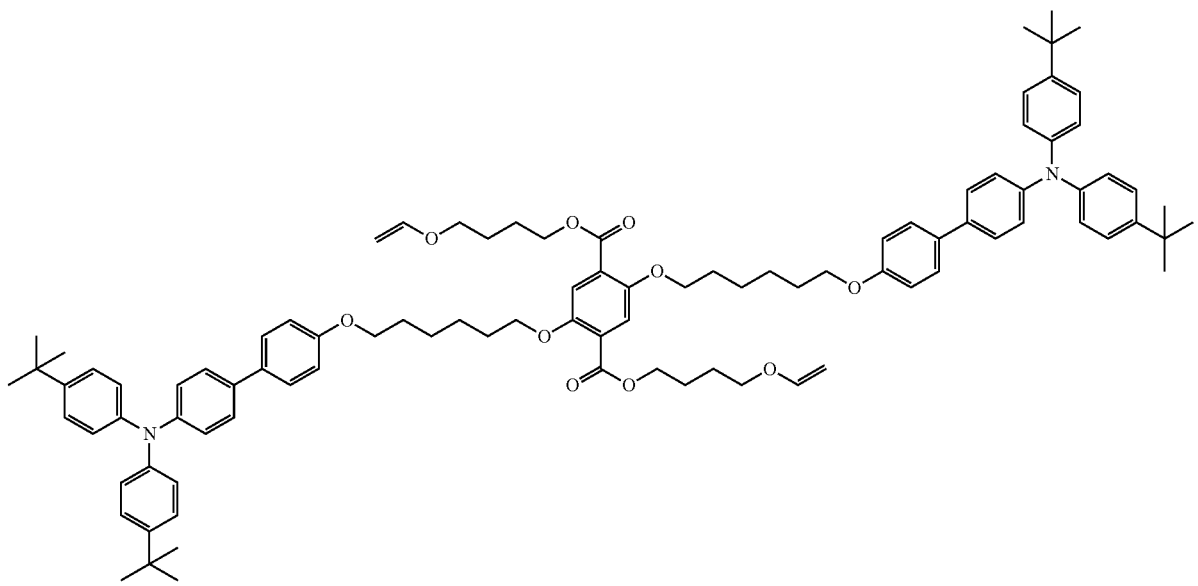 [SMILES: C=COCCCCOC(=O)c1cc(OCCCCCCOc2ccc(-c3ccc(N(c4ccc(C(C)(C)C)cc4)c4ccc(C(C)(C)C)cc4)cc3)cc2)c(C(=O)OCCCCOC=C)cc1OCCCCCCOc1ccc(-c2ccc(N(c3ccc(C(C)(C)C)cc3)c3ccc(C(C)(C)C)cc3)cc2)cc1]

Synthesis of Compound 5

N,N'-Dicyclohexylcarbodiimide (0.10 g, 0.50 mmol), was added to a stirred solution of compound 4 (0.25 g, 0.20 mmol) and 4-dimethylaminopyridine (2.4 mg, 0.02 mmol) in dry dichloromethane (7 mL) at 0° C. The mixture was then stirred under argon at 0° C. for 1 h, after which the 1,4-butanediol vinyl ether (0.09 g, 0.79 mmol) in dry dichloromethane (3 mL) was added and the reaction mixture was allowed to warm to room temperature and left to stir under argon for 18 h. After which the solution was diluted with dichloromethane (60 mL) and then washed with saturated NaHCO$_3$ (2×50 mL) and water (50 mL). The organic layer was then dried (MgSO$_4$), filtered and the solvent was removed under reduced pressure. The crude product was purified by flash chromatography (10% ethyl acetate in hexane). This yielded the desired product as a white solid (0.10 g, 0.069 mmol, 35%). $^1$H NMR (400 MHz, CDCl$_3$), δ=1.32 (36H, s, CH$_3$), 1.53-1.57 (8H, m, CH$_2$), 1.80-1.89 (16H, m, CH$_2$), 3.73 (4H, t, J=6.0 Hz, CH$_2$), 3.97-4.04 (10H, m, CH$_2$ & =CH$_2$), 4.16 (2H, dd, J=14.4, 2.0 Hz, =CH$_2$), 4.34 (4H, t, J=6.2 Hz, CH$_2$), 6.46 (2H, dd, J=14.4, 6.8 Hz, =CH), 6.94 (4H, br d, J=8.8 Hz, Ar—H), 7.05 (8H, br d, J=8.5 Hz, Ar—H), 7.10 (4H, br d, J=8.7 Hz, Ar—H), 7.26 (8H, br d, J=8.5 Hz, Ar—H), 7.35 (2H, s, Ar—H), 7.40 (4H, br d, J=8.7 Hz, Ar—H), 7.47 (4H, br d, J=8.8 Hz, Ar—H); MS (MALDI+): m/z calculated for [M+H]$^+$=1457.8, found 1457.7.

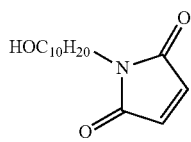

Synthesis of N-decanol-maleimide

A solution of 10-bromo-1-decanol (2.94 g, 12.4 mmol) in dry DMF (10 mL) was added to a stirred suspension of a mixture of the endo/exo furan protected maleimide (2.05 g, 12.4 mmol) and K$_2$CO$_3$ (1.72 g, 12.4 mmol) in dry DMF (40 mL) under argon. The reaction mixture was then stirred at 50° C. under argon for 16 h (reaction turned dark red in colour overnight). After which the reaction mixture was poured into water (200 mL) and was extracted with ethyl acetate (3×100 mL). The combined organics were washed with water (200 mL) and brine (2×100 mL). The organic layer was then dried (MgSO$_4$), filtered and the solvent was removed under reduced pressure. The oily residue was triturated with the aid sonication under hexane which was then decanted off. This process was repeated twice to remove any unreacted bromo-decanol. The oily residue was then dissolved in diethyl ether and filtered. The filtrate was evaporated under reduced pressure to yield the product as a colourless oil which solidified on standing overnight at room temperature (2.32 g, 7.2 mmol, 58%).

The mixture of endo/exo N-decanol-furan protected maleimide (1.15 g, 3.6 mmol) was heated to reflux in toluene (20 mL) and stirred at reflux for 18 h. After which the solvent was removed under reduced pressure and the crude product was purified by flash chromatography (30-50% ethyl acetate in hexane). This yielded the product as a white solid (0.52 g, 2.1 mmol, 58%). $^1$H NMR (400 MHz, CDCl$_3$), δ=1.22-1.35 (12H, m, CH$_2$), 1.54-1.61 (4H, m, CH$_2$), 3.48-3.52 (2H, m, CH$_2$), 3.63 (2H, t, J=6.6 Hz, CH$_2$), 6.68 (2H, s, =CH).

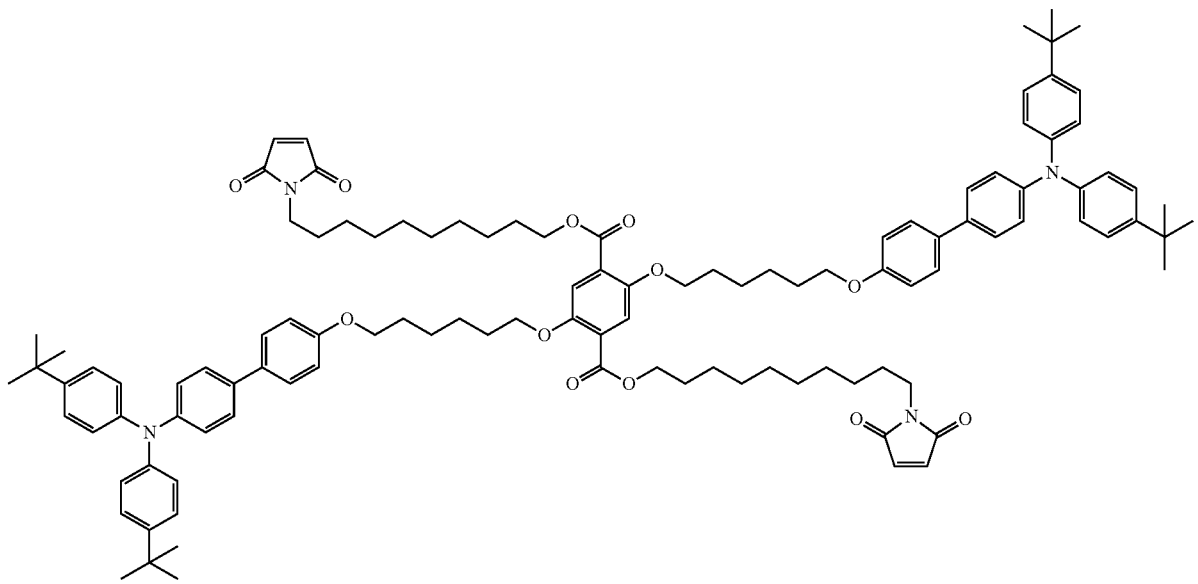 [SMILES: CC(C)(C)c1ccc(N(c2ccc(-c3ccc(OCCCCCCOc4cc(C(=O)OCCCCCCCCCCN5C(=O)C=CC5=O)c(OCCCCCCOc5ccc(-c6ccc(N(c7ccc(C(C)(C)C)cc7)c7ccc(C(C)(C)C)cc7)cc6)cc5)cc4C(=O)OCCCCCCCCCCN4C(=O)C=CC4=O)cc3)cc2)c2ccc(C(C)(C)C)cc2)cc1]

Synthesis of Compound 6

N,N'-Dicyclohexylcarbodiimide (0.10, 0.50 mmol), was added to a stirred solution of compound 4 (0.25 g, 0.20 mmol) and 4-dimethylaminopyridine (4.8 mg, 0.04 mmol) in dry dichloromethane (7 mL) at 0° C. The mixture was then stirred under argon at 0° C. for 1 h, after which the N-decanol-maleimide (0.13 g, 0.50 mmol) in dry dichloromethane (3 mL) was added and the reaction mixture was allowed to warm to room temperature and left to stir under argon for 18 h. The solution was then diluted with dichloromethane (60 mL) and then washed with saturated NaHCO$_3$ (2×50 mL) and water (50 mL). The organic layer was then dried (MgSO$_4$), filtered and the solvent was removed under reduced pressure. The crude product was purified by flash chromatography (20% ethyl acetate in hexane) which yielded the product as yellow solid (20 mg, 0.012 mmol, 6%). $^1$H NMR (400 MHz, CDCl$_3$), δ=1.24-1.29 (24H, m, CH$_2$), 1.32 (36H, s, CH$_3$), 1.53-1.58 (10H, m, CH$_2$), 1.71-1.87 (14H, m, CH$_2$), 3.47-3.50 (4H, m, CH$_2$), 3.98-4.04 (8H, m, CH$_2$), 4.29 (4H, t, J=6.7 Hz, CH$_2$), 6.65 (4H, s, =CH), 6.94 (4H, br d, J=8.8 Hz, Ar—H), 7.05 (8H, br d, J=8.7 Hz, Ar—H), 7.10 (4H, br d, J=8.6 Hz, Ar—H), 7.26 (8H, br d, J=8.7 Hz, Ar—H), 7.35 (2H, s, Ar—H), 7.40 (4H, br d, J=8.6 Hz, Ar—H), 7.48 (4H, br d, J=8.8 Hz, Ar—H); MS (MALDI+): m/z calculated for [M+H]$^+$= 1732.0, found 1731.9.

Cross Linked Hole Only Device

In order to demonstrate the properties of the single carrier hole only devices have been fabricated with the crosslinkable hole transport materials 5 (vinyl ether cross linker) and 6 (maleimide cross linker) that were synthesised according to the protocols described above. The structure of the devices was ITO/PEDOT:PSS (50 nm)/Hole transport material (65 nm)/Au. The high work function of the gold cathode ensures that there is no electron injection into the organic layer, so that the current through the device is due to the transport of holes only.

The hole transport layer consisted of a mixture of hole transport material with maleimide crosslinker unit 6 and hole transport material with vinyl ether crosslinker unit 5 blended in the ratio 1:1.

The solution processable PEDOT:PSS and hole transport layers were deposited on a pre-patterned glass/ITO substrate by spin coating. Spin coating the hole transport material from a 20 mg/mL toluene solution at 2500 rpm for 60 seconds delivered a thin film with a thickness of 75 nm.

After spin coating, the deposited film of hole transport material 5 and 6 was exposed to a metal halide lamp with broad emission from 280-450 nm (Dymax BlueWave 200) at a power density of 5 W/cm$^2$ for 20 seconds in an argon atmosphere to crosslink the material. After crosslinking, the device was spin rinsed with toluene in order to remove any uncrosslinked material, leaving an insoluble 65 nm film of hole transport material. The gold cathode was subsequently deposited by thermal evaporation.

FIG. 1 shows current voltage data for this simple hole only device, along with the data for a hole only device where the hole transporting material is poly(9-vinyl carbazole) (PVK) for comparison. The line for PVK starts lower and ends higher on the right hand side. PVK is a commercially available polymer with hole transporting properties commonly used as a host material in OLED devices. The current flow measured through the hole transport material is due only to the transport of holes through the organic layer as a result of the device architecture, and exceeds the current flow through the comparable PVK device at low voltages. This demonstrates that crosslinking of these materials results in an insoluble film suitable for application as a hole transport material in OLED devices.

A preferred aspect of the invention will now be further described below. All elements of the preceding aspects apply equally to the following aspect, although some of the labeling has been adapted for conciseness.

There is provided a compound of the formula:

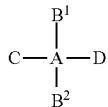

wherein:

A represents a phenyl group, a naphthyl group, a biphenyl group or two phenyl groups linked by a $C_1$-$C_8$ alkyl chain;

$B^1$ and $B^2$ in each occurrence are independently of the structure -$(G^1)_n$-L-$(G^2)_m$—X C is of the structure -$(G^1)_n$-M-$(G^2)_m$-E D is of the structure -$(G^1)_n$-M-$(G^2)_m$-F wherein:

$G^1$ and $G^2$ in each occurrence are independently selected from —O—, —C(O)O— and —CH$_2$O—, m and n in each occurrence are independently selected from 0 or 1;

L in each occurrence is a $C_2$-$C_{14}$ straight chain alkyl group; and

M in each occurrence is a $C_1$-$C_{14}$ straight chain alkyl group; and

X in each occurrence is an independently selected cross linkable group;

E comprises a charge transport group;

F comprises a charge transport group or light emitter group; and wherein the charge transport group E does not contain a fluorene group other than those that form part of a spirobifluorenearylamine motif.

Preferably A is a phenyl group, a naphthyl group, a biphenyl group. Preferably it is a 1,2,4,5 substituted phenyl group, with the C and D groups para to each other.

Preferably X is independently selected from the group consisting of alkene cross-linking groups, thiols and oxetanes. The most preferred X is independently selected from methacrylate, ethacrylate, ethylmaleato, ethylfumarato, N-maleimido, vinyloxy, alkylvinyloxy, vinylmaleato, vinylfumarato, N-(2-vinyloxymaleimido), 1,4-pentadien-3-yl and 1,4-cyclohexadienyl groups.

E is a charge transport group, i.e. either a hole transporting group or an electron-transporting group. A hole transporting group is any material which allows a flow of holes through the material, whereas an electron-transporting group is any material which allows a flow of electrons through the material. Electron transport materials typically comprise electron deficient aromatic groups/moieties and hole transport materials typically comprise electron rich aromatic groups/moieties. Such terms are well known in the art and the skilled person would readily identify suitable moieties to impact such functionality to a compound. For example, U.S. Pat. No. 9,112,157 describes a range of hole transporting functionalities and WO2006127315 describes electron transporting materials.

Similarly, F may be a charge transporting group, in which case it can be independently selected from the same structures disclosed herein for such structures, or F may be a light-emitting group. When E and F are both charge-transporting groups, preferably they are identical. Preferably F is a light emitting group and E is a charge transporting group.

The preferred light emitting group for F the structure:

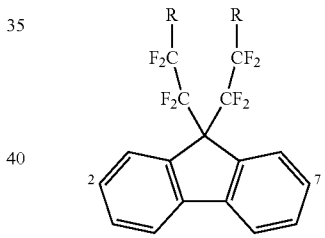

wherein R are identical and are selected from the group consisting of straight chain or branched achiral $C_1$-$C_{14}$ alkyl, $C_1$-$C_{14}$ haloalkyl (preferably fluoroalkyl), $C_2$—C alkenyl group, optionally wherein 1, 2, 3, 4 or 5 CH$_2$ groups are replaced by an oxygen provided that no acetal, ketal, peroxide or vinyl ether is present in the R group, and wherein the F group is connected into the D structure at the C2 or C7 carbon.

Preferred hole transporting groups for E and F are independently selected from a group comprising a triaryl amine, such as a triphenylamine or a spirobifluorenearylamine, a 3,6-carbazole, a, 2,7-carbazole or a 1,3,6,8-carbazole.

Preferred electron transporting groups for E and F are independently selected from a group comprising one or more of benzimidazole, oxadiazole, triazole, phenanthroline, 2-phenylpyridine, 1,3,5-triazine, thiadiazole or (8-hydroxylquinoline)aluminium. Preferably E and F are independently selected from a group comprising one to six of benzimidazole, oxadiazole, triazole, phenanthroline, 2-phenylpyridine, 1,3,5-triazine, thiadiazole or (8-hydroxylquinoline)aluminium.

The above compounds may be formed into a network polymer by exposure of the compound to radiation, preferably ultraviolet light. The compounds or polymer may also be incorporated into a device, such as an OLED device, OPV device or OFET device.

Such a device may be made from the compounds using a method including:
i) dissolving a compound as described herein in a suitable organic solvent;
ii) depositing the resultant solution on a substrate;
iii) removing the solvent under evaporation, optionally under reduced pressure to form a film; and
iv) exposing the resultant film to radiation, optionally wherein the radiation is ultraviolet light.

The invention claimed is:
1. A compound of the formula

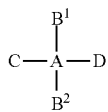

wherein:
A represents a phenyl group, a naphthyl group, a biphenyl group or two phenyl groups linked by a $C_1$-$C_8$ alkyl chain, wherein A is unsubstituted with the exception of substituents $B^1$, $B^2$, C and D;
$B^1$ and $B^2$ in each occurrence are independently selected side chains of the structure

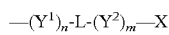

wherein:
$Y^1$ and $Y^2$ in each occurrence are independently selected from O, $CO_2$— and $CH_2O$;
m and n in each occurrence are independently selected from 0 or 1;
L in each occurrence is a $C_2$-$C_{14}$ straight chain alkyl group; and
X in each occurrence is an independently selected cross linkable group;
C is a side chain of the structure $(Z^1)_p$-M-$(Z^2)_q$-E
wherein:
$Z^1$ and $Z^2$ are independently selected from O, $CO_2$— and $CH_2O$;
p and q in each occurrence are independently selected from 0 or 1;
M is a $C_1$-$C_{14}$ straight chain alkyl group; and
E comprises a charge transport group;
D is a side chain of the structure —$(W^1)_r$—N—$(W^2)_s$—F
wherein:
$W^1$ and $W^2$ are independently selected from O, $CO_2$— and $CH_2O$;
r and s in each occurrence are independently selected from 0 or 1;
N is a $C_1$-$C_{14}$ straight chain alkyl group; and
F comprises a charge transport group or light emitter group;
and wherein the charge transport group E does not contain a fluorene group other than those that form part of a spirobifluorenearylamine motif.

2. A compound according to claim 1 wherein the group X of $B^1$ and/or $B^2$ is an alkene cross linking group.

3. A compound according to claim 1 wherein the group E and/or F is a hole transporting group that comprises a triarylamine hole transport motif or a carbazole hole transport motif.

4. A compound according to claim 3 wherein the group E and/or F is a hole transporting group that comprises a triaryl amine.

5. A compound according to claim 3 wherein the group E and/or F is a hole transporting group that can be described by the general formula

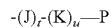

wherein J is a phenyl group, a benzyl group, a biphenyl group, a 2,2'-bithiophene group, a fused thiophene group or thiophene, t is 0 or 1, K is a hole transporting motif selected from triarylamine, 3,6-carbazole, 2,7-carbazole or 1,3,6,8-carbazole linked to adjacent members of the hole transporting group via a covalent bond, a phenyl group, a fused thiophene group or thiophene, u is an integer from 1 to 10, and P is a chain terminating group selected from hydrogen, $C_1$-$C_8$ straight or branched alkyl, phenyl, $C_1$-$C_8$ straight or branched alkyl substituted phenyl, or $C_1$-$C_8$ straight or branched alkyl substituted biphenyl.

6. A compound according to claim 1 wherein the group E and/or F is an electron transporting group that comprises an electron transporting motif selected from benzimidazole, oxadiazole, triazole, phenanthroline, 2-phenylpyridine, 1,3, 5-triazine, thiadiazole or (8-hydroxylquinoline)aluminium.

7. A compound according to claim 6 wherein the group E is an electron transporting group that comprises a chain comprising from one to ten electron transporting motifs selected from benzimidazole, oxadiazole, triazole, phenanthroline, 2-phenylpyrimidine, 1,3,5-triazine or thiadiazole mutually connected by covalent bonds, phenyl or $C_1$-$C_5$ heterocycle linkages, and at a terminus of the group E or F, respectively, i) a $C_1$-$C_8$ alkyl group, ii) an optionally substituted phenyl group or iii) an optionally substituted biphenyl group, wherein the optional substituent is a $C_1$-$C_8$ alkyl group.

8. A compound according to claim 6 wherein the group E and/or F the electron transport motif is a straight chain of formula:

wherein $Ar^1$ is an independently selected phenyl or biphenyl group;
m=0 or 1;
q=1;
Het in each occurrence is a covalent bond or a heterocycle selected from benzimidazole, oxadiazole, triazole, phenanthroline, 2-phenylpyrimidine, 1,3,5-triazine and thiadiazole provided that at least one heterocycle selected from benzimidazole, oxadiazole, triazole, phenanthroline, 2-phenylpyrimidine, 1,3,5-triazine and thiadiazole is present;
$Ar^2$ is in each occurrence selected from a covalent bond, a phenyl group, a $C_1$-$C_5$ heterocycle;
n is an integer from 1 to 10;
$Ar^3$ is i) H or a $C_1$-$C_8$ alkyl group, ii) an optionally substituted phenyl group or iii) an optionally substituted biphenyl group, wherein the optional substituent in cases ii) and iii) is a $C_1$-$C_8$ alkyl group;
provided that no more than ten benzimidazole, oxadiazole, triazole, phenanthroline, 2-phenylpyrimidine, 1,3, 5-triazine and thiadiazole groups are present in each of the groups E and F.

9. A compound according to claim 1 wherein E and F are identical.

10. A compound according to claim 1 wherein F is a light emitting group.

11. A compound according to claim 10 wherein F is a light emitter group comprising a group FL of the structure

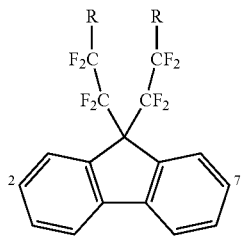

wherein the R groups of each FL moiety are identical and are selected from the group consisting of straight chain or branched achiral $C_1$-$C_{14}$ alkyl, $C_1$-$C_{14}$ haloalkyl, $C_1$-$C_{14}$ fluoroalkyl, $C_2$-$C_{14}$ alkenyl group, optionally wherein 1, 2, 3, 4 or 5 $CH_2$ groups are replaced by an oxygen provided that no acetal, ketal, peroxide or vinyl ether is present in the R group.

12. A network polymer formed by exposure of a compound according to claim 1 to ultraviolet light or other radiation.

13. The compound of claim 1 incorporated into a device.

14. The compound of claim 13 wherein the device is an OLED device, OPV device or OFET device.

15. A method for making a device according to claim 13 comprising the steps of:
   i) dissolving the compound in a suitable organic solvent to form a solution;
   ii) depositing the solution prepared in step (i) on a substrate;
   iii) removing the solvent under evaporation, optionally under reduced pressure to form a film; and
   iv) exposing the film prepared in step (iii) to radiation, optionally wherein the radiation is ultraviolet light.

16. A compound according to claim 1 wherein the group X of $B^1$ and/or $B^2$ is a thiol.

17. A compound according to claim 1 wherein the group X of $B^1$ and/or $B^2$ is an oxetane.

18. A compound according to claim 5 wherein the triarylamine is a triphenylamine or a spirobifluorenearylamine.

* * * * *